United States Patent
Reisman et al.

(10) Patent No.: US 9,862,696 B2
(45) Date of Patent: Jan. 9, 2018

(54) SYNTHETIC ROUTE TO ANHYDRORYANODOL, RYANODOL AND STRUCTURAL ANALOGUES

(71) Applicant: CALIFORNIA INSTITUTE OF TECHNOLOGY, Pasadena, CA (US)

(72) Inventors: Sarah Reisman, South Pasadena, CA (US); Kangway V. Chuang, Pasadena, CA (US); Chen Xu, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/381,595

(22) Filed: Dec. 16, 2016

(65) Prior Publication Data

US 2017/0174648 A1    Jun. 22, 2017

Related U.S. Application Data

(60) Provisional application No. 62/269,760, filed on Dec. 18, 2015.

(51) Int. Cl.
| | |
|---|---|
| *C07D 309/30* | (2006.01) |
| *C07C 43/23* | (2006.01) |
| *C07C 49/577* | (2006.01) |
| *C07C 49/753* | (2006.01) |
| *C07D 309/32* | (2006.01) |
| *C07C 43/315* | (2006.01) |
| *C07C 49/743* | (2006.01) |

(52) U.S. Cl.
CPC .......... *C07D 309/30* (2013.01); *C07C 43/23* (2013.01); *C07C 43/315* (2013.01); *C07C 49/577* (2013.01); *C07C 49/743* (2013.01); *C07C 49/753* (2013.01); *C07D 309/32* (2013.01)

(58) Field of Classification Search
CPC .................................................. C07D 309/30
See application file for complete search history.

(56) References Cited

PUBLICATIONS

Chuang, K.V., et al. "A 15-step synthesis of (+)-ryanodol." Science. (Aug. 26, 2016), vol. 353, Issue 6302. pp. 912-915.*
Belanger et al., "Total Synthesis of Ryanodol", Can. J. Chem., Dec. 1979, 57, 3348-3354.
Chuang et al., "A 15-step Synthesis of (+)-Ryanodol", Science, Aug. 26, 2016, 353(6302), 912-915.
Deslongchamps et al., "The total synthesis of (+)-ryanodol. Part I. General strategy and search for a convenient diene for the construction of a key tricyclic intermediate", Can. J. Chem., Jan. 1990, 68, 115-126.
Deslongchamps et al., "The total synthesis of (+)-ryanodol. Part IV. Preparation of (+)-ryanodol from (+)-anhydroryanodol", Can. J. Chem., Jan. 1990, 68, 186-192.
Deslongchamps et al., "The total synthesis of (+)-ryanodol. Part III. Preparation of (+)-anhydroryanodol from a key pentacyclic intermediate", Can. J. Chem., Jan. 1990, 68, 153-185.
Deslongchamps et al., "The total synthesis of (+)-ryanodol. Part II. Model Studies for rings B and C of (+)-anhydroryanodol. Preparation of a key pentacyclic intermediate", Can. J. Chem., 1990, 68, 127-152.
Koshimizu et al., "Unified Total Synthesis of 3-epi-Ryanodol, Cinnzeylanol, Cinncassiols A and B, and Structural Revision of Natural Ryanodol and Cinnacasol", Angew Chem Int Ed., Feb. 2016, 55, 2493-2497.
Masuda et al., "Asymmetric Total Synthesis of (+)-Ryanodol and (+)-Ryanodine", Chemistry, Jan. 2016, 22, 230-236.
Nagatomo et al., "Symmetry-Driven Strategy for the Assembly of the Core Tetracycle of (+)-Ryanodine: Synthetic Utility of a Cobalt-Catalyzed Olefin Oxidation and α-Alkoxy Bridgehead Radical Reaction", Chemistry, Jan. 2016, 22, 222-229.
Nagatomo et al., "Total Synthesis of Ryanodol", J. Am. Chem. Soc., Apr. 2014, 136, 5916-5919.
Sutko et al., "The pharmacology of ryanodine and related compounds", Pharmacol. Rev., Mar. 1997, 49, 1, 53-98.
Waterhouse et al., "Structural Aspects of Ryanodine Action and Selectivity", J. Med. Chem., Apr. 1987, 30, 710-716.
Welch et al., "Structural Determinants of High-Affinity Binding of Ryanoids to the Vertebrate Skeletal Muscle Ryanodine Receptor: A Comparative Molecular Field Analysis", Biochemistry, May 1994, 33, 6074-6085.
Welch et al., "Structural Components of Ryanodine Responsible for Modulation of Sarcoplasmic Reticulum Calcium Channel Function", Biochemistry, Mar. 1997, 36, 2939-2950.
Ke et al., "Mechanism and Reactivity of Rh-Catalyzed Intermolecular [5+1] Cycloaddition of 3-Acyloxy-1,4-Enyne (ACE) and CO: A Computational Study", Chin. Chem. Lett., Jun. 2015, 26(6), 730-734.
Ruest et al., "Ryanoids and related compounds. A total synthesis of 3-epiryanodine", Canadian Journal of Chemistry, 1993, vol. 71, No. 5, 634-638.

* cited by examiner

*Primary Examiner* — Noble Jarrell
*Assistant Examiner* — John S Kenyon
(74) *Attorney, Agent, or Firm* — Baker & Hostetler LLP

(57) ABSTRACT

This disclosure is related to methods for producing anhydroryanodol, ryanodol, or analogs thereof and novel compounds prepared thereby.

32 Claims, No Drawings

SYNTHETIC ROUTE TO ANHYDRORYANODOL, RYANODOL AND STRUCTURAL ANALOGUES

CROSS REFERENCE TO RELATED APPLICATIONS

This application claims the priority of U.S. Provisional Patent Application No. 62/269,760, filed Dec. 18, 2015, which application is incorporated by reference herein.

GOVERNMENT RIGHTS

This invention was made with government support under Grant No. DGE1144469 awarded by the National Science Foundation and under Grant No. GM097582 awarded by the National Institutes of Health. The government has certain rights in the invention.

TECHNICAL FIELD

This disclosure is related to methods for producing anhydroryanodol, ryanodol, and analogues thereof.

BACKGROUND

Terpenes are a large and structurally diverse family of natural products that range from simple hydrocarbons associated with flavors and fragrances, to complex, highly oxidized polycyclic molecules such as the anti-malarial drug artemisinin, and the anticancer compounds ingenol and taxol. Although terpenes are isolated from natural sources, it can be challenging to translate their biological activity into a practical application. In some cases, the hurdle is low natural abundance; other times, it is the difficulty encountered by chemists seeking to precisely edit a terpene's molecular structure in order to improve its drug-like properties or interrogate its role in modulating disease pathways. The development of concise chemical syntheses of terpenes can transform the ability to use these molecules and their synthetic derivatives as biological probes or as lead compounds for the development of new medicines. Furthermore, these scientific efforts often innovate chemical reactivity or synthetic design concepts.

The natural product ryanodine (1) and its hydrolysis product ryanodol (2) are among the most highly oxidized and synthetically challenging diterpenoids reported to date.

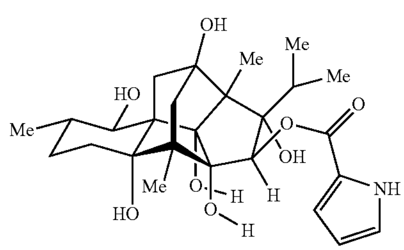

(+)-ryanodine (1)

-continued 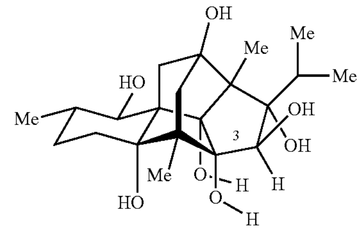 (+)-ryanodol (2)

Isolated from the tropical shrub Ryania speciosa Vahl in connection with its insecticidal properties, ryanodine is the namesake ligand of the ryanodine receptors (RyRs), an important family of ion channels that regulate intracellular $Ca^{2+}$ release and play a critical role in signal transduction. In mammalian cells, these receptors exist in multiple isoforms (RyR1, RyR2, and RyR3) that serve to mediate both movement and cognitive function. Mutations of RyRs are associated with genetic diseases such as malignant hyperthermia and central core disease, while altered expression of RyR2 and RyR3 has been associated with the pathogenesis of neurodegenerative disorders such as Alzheimer's disease. Ryanodine binds with high affinity to the conducting state of RyRs, exerting concentration dependent modulation of $Ca^{2+}$ release: at nanomolar concentrations, ryanodine locks RyRs in an open, subconductance state, whereas at higher concentrations, ryanodine causes closure of the channels. The deacylated compound ryanodol binds with lower affinity than 1 to mammalian RyRs; however, it still induces a subconductance state and has been reported as a reversible probe of RyR-mediated $Ca^{2+}$ release in cells.

Since the initial reports describing the isolation of ryanodine from Ryania, a number of congeners (known as ryanoids) that vary in oxidation pattern have been isolated. Whereas ryanodol—the compound obtained by hydrolysis of ryanodine has not yet been isolated directly from a natural source, the closely related compound C3-epi-ryanodol (4) was isolated by Gonzaléz-Coloma from Persea indica.

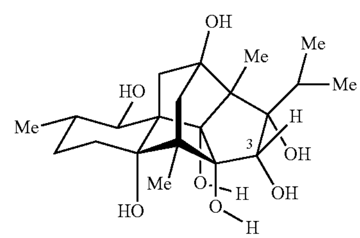

(+)-3-epi-ryanodol (4)

Indeed, due to their structural similarities, C3-epi-ryanodol (4) was initially erroneously reported to be ryanodol (2); however, the structure of the Coloma-Gonzalez isolate was recently reassigned through the synthetic efforts of Inoue. (M. Koshimizu et al, *Angew Chem. Int. Ed. Engl.* 55, 2493-2497 (2016)). These subtle differences in structure exert a pronounced effect on RyR-binding: C3-epi-ryanodine (5), prepared from 4, binds 100 fold more weakly to RyRs than 1. (W. Welch et al. *Biochemistry* 36, 2939-2950 (1997)).

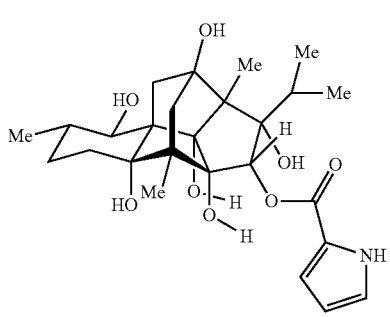

(+)-3-epi-ryanodine (5)

Given the biological importance of the RyRs, the ryanoids have been the focus of both total synthesis and derivatization efforts. (A. Belanger et al. *Can. J. Chem.* 57, 3348-3354 (1979); P. Deslongchamps et al. *Can. J. Chem.* 68, 115-126 (1990); P. Deslongchamps et al. *Can. J. Chem.* 68, 127-152 (1990); P. Deslongchamps et al. *Can. J. Chem.* 68, 153-185 (1990); P. Deslongchamps et al. *Can. J. Chem.* 68, 186-192 (1990); M. Nagatomo et al. *J. Am. Chem. Soc.* 136, 5916-5919 (2014); M. Nagatomo et al. *Chemistry* 22, 222-229 (2016); K. Masuda et al. *Chemistry* 22, 230-236 (2016); A. L. Waterhouse, et al. *J. Med. Chem.* 30, 710-716 (1987); W. Welch et al. *Biochemistry* 33, 6074-6085 (1994); J. L. Stuko et al. *Pharmacol. Rev.* 49, 53-98 (1997)). These synthetic efforts, however, include up to 41 steps.

Alternative routes of preparing (+)-ryanodol and ryanodol, as well as derivatives thereof, are needed

SUMMARY

The present disclosure provides methods for preparing compounds of Formula (I):

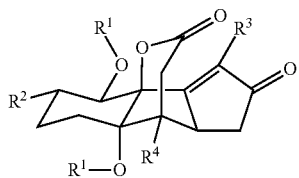

(I)

comprising subjecting compounds of Formula (II):

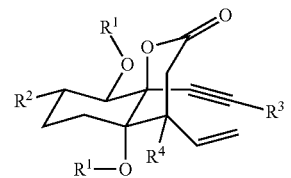

(II)

to a source of carbon monoxide in the presence of a catalyst, for a time and at a temperature sufficient to produce the compounds of Formula (I); wherein each $R^1$ is a reductively labile oxygen protecting group or an acid labile oxygen protecting group; $R^2$ is $C_{1-6}$alkyl; $R^3$ is $C_{1-6}$alkyl; and $R^4$ is $C_{1-6}$alkyl.

Also provided are compounds including:

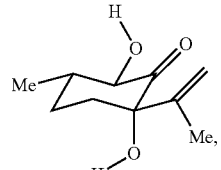

12

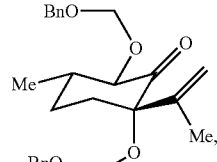

13

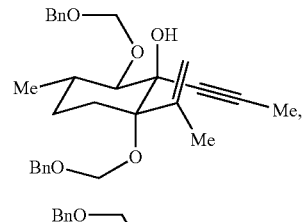

Si-1

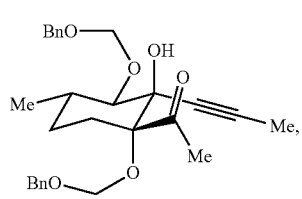

14

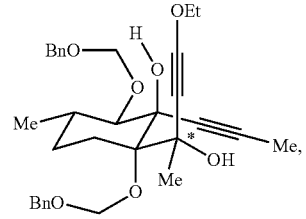

Si-2

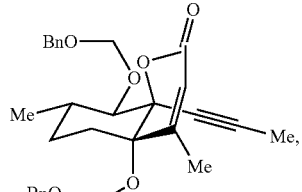

15

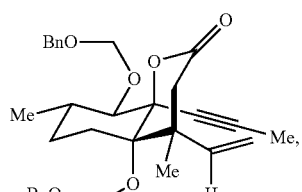

16

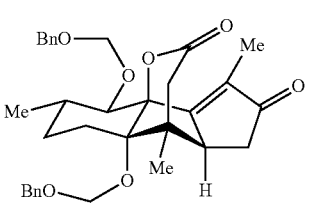

17

-continued

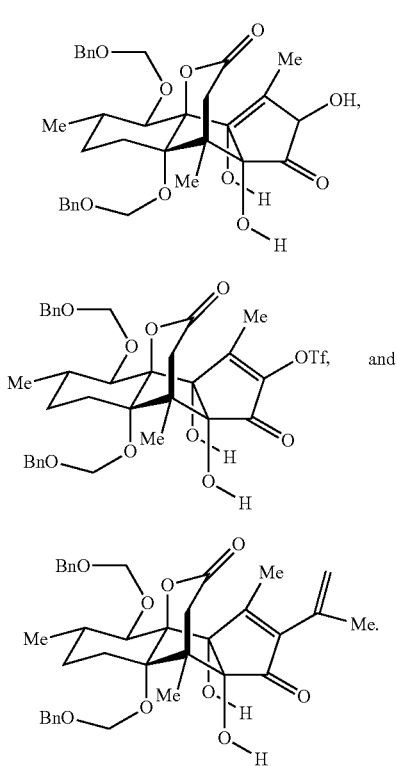

DETAILED DESCRIPTION OF ILLUSTRATIVE EMBODIMENTS

The disclosure may be more fully appreciated by reference to the following description, including the following glossary of terms and the concluding examples. It is to be appreciated that certain features of the disclosed compositions and methods which are, for clarity, described herein in the context of separate aspects, may also be provided in combination in a single aspect.

In the following descriptions of exemplary embodiments of the present invention, all references, including publications, patent applications, and patents, cited herein are incorporated by reference into this application to the same extent as if each reference were individually and specifically indicated to be incorporated by reference and were set forth in its entirety herein.

Conversely, various features of the disclosed compositions and methods that are, for brevity, described in the context of a single aspect, may also be provided separately or in any subcombination.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a," "an," and "the" are not limited to one element but instead should be read as meaning "at least one."

When a value is expressed as an approximation by use of the descriptor "about" it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about". In other cases, the gradations used in a series of values may be used to determine the intended range available to the term "about" for each value. Where present, all ranges are inclusive and combinable. That is, references to values stated in ranges include every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

When a range of carbon atoms is used herein, for example, $C_{1-6}$, all ranges, as well as individual numbers of carbon atoms are encompassed. For example, "$C_{1-3}$" includes $C_{1-3}$, $C_{1-2}$, $C_{2-3}$, $C_1$, $C_2$, and $C_3$.

The term "alkyl" refers to a straight- or branched-chain alkyl group having. Alkyl moieties preferably have from 1 to 6 carbon atoms ("$C_{1-6}$"), in the chain. Examples of alkyl groups include methyl (Me, $C_1$alkyl) ethyl (Et, $C_2$alkyl), n-propyl ($^n$Pr, $C_3$alkyl), isopropyl ($^i$Pr, $C_3$alkyl), butyl (Bu, $C_4$alkyl), isobutyl ($^i$Bu, $C_4$alkyl), sec-butyl ($^s$Bu, $C_4$alkyl), tert-butyl ($^t$Bu, $C_4$alkyl), pentyl ($C_5$alkyl), isopentyl ($C_5$alkyl), tert-pentyl ($C_5$alkyl), hexyl ($C_6$alkyl), isohexyl ($C_6$alkyl), and groups that in light of the ordinary skill in the art and the teachings provided herein would be considered equivalent to any one of the foregoing examples.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(+)" is used to designate a racemic mixture where appropriate. "Diastereoisomers" are stereoisomers that have at least two asymmetric atoms, but which are not mirror images of each other. The absolute stereochemistry is specified according to the Cahn-Ingold-Prelog R-S system. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions, and methods are meant to include all such possible isomers, including single stereoisomers, racemic mixtures, diastereomeric mixtures, and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, it is intended that the compounds may include both E and Z geometric isomers.

A direct and concise strategy is described to access the central ryanoid ring system to prepare (+)-ryanodol (2) in only 15 steps from commercially available starting materials. Previously inaccessible ryanoid derivatives can also be prepared using methods described herein.

Synthesis of Compounds of Formula (I)

Methods for preparing compounds of Formula (I) from compounds of Formula (II) are provided, wherein each $R^1$ is a reductively labile oxygen protecting group or an acid labile oxygen protecting group, $R^2$ is $C_{1-6}$alkyl, $R^3$ is $C_{1-6}$alkyl, and $R^4$ is $C_{1-6}$alkyl.

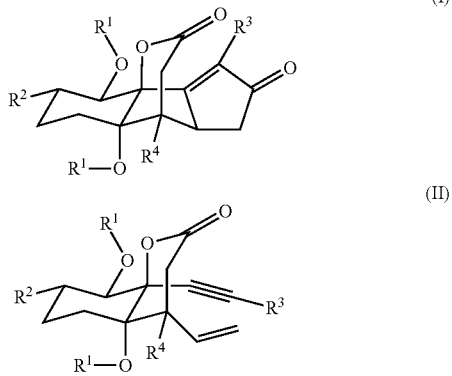

According to the disclosure, each $R^1$ is a reductively labile oxygen protecting group or an acid labile oxygen protecting group. Exemplary reductively labile oxygen protecting groups and acid labile oxygen protecting groups are known in the art. See, e.g., Wuts and Greene, "Greene's Protective Groups in Organic Synthesis," Fourth Ed., John Wiley & Sons, Inc., 2007. In some embodiments, each $R^1$ is benzyloxymethyl (BnO-CH$_2$—). In other embodiments, each $R^1$ is a trialkylsilylalkoxy methyl moiety, for example, a trimethylsilylethoxy methyl ("SEM") moiety. In other embodiments, each $R^1$ is an alkoxymethyl, for example, a methoxymethyl ("MOM") moiety.

According to the disclosure, and $R^2$ is $C_{1-6}$alkyl, for example, methyl, ethyl, propyl, iso-propyl, and the like. Preferably, $R^2$ is $CH_3$.

According to the disclosure $R^3$ is $C_{1-6}$alkyl. Preferably, $R^3$ is $CH_3$. In other embodiments, $R^3$ is ethyl. In other embodiments, $R^3$ is propyl. In still further embodiments, $R^3$ is butyl. In yet other embodiments, $R^3$ is pentyl. In further embodiments, $R^3$ is hexyl.

According to the disclosure $R^4$ is $C_{1-6}$alkyl. Preferably, $R^4$ is $CH_3$. In other embodiments, $R^4$ is ethyl. In other embodiments, $R^4$ is propyl. In still further embodiments, $R^4$ is butyl. In yet other embodiments, $R^4$ is pentyl. In further embodiments, $R^4$ is hexyl.

According to the methods of the disclosure, the compounds of formula (II) are subjected to a source of carbon monoxide in the presence of a catalyst, preferably in an organic solvent, for a time and at a temperature sufficient to produce the compounds of Formula (I).

In some embodiments, the source of carbon monoxide is gaseous CO, $Co_2(CO)_8$, $Mo(CO)_6$, or $Mo(CO)_3(DMF)_3$. An excess of the carbon monoxide source is preferable, with about 1.1 to about 3 equivalents, for example, about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or about 3.0 equivalents of the carbon monoxide source. In some embodiments, about 1.2 equivalents of the carbon monoxide source, preferably $Co_2(CO)_8$, $Mo(CO)_6$, or $Mo(CO)_3(DMF)_3$, is used. If gaseous CO is employed, a very large excess of gaseous CO can be used as the carbon monoxide source.

In preferred embodiments, the catalyst used to convert the compounds of formula (II) to the compounds of formula (I) is a rhodium catalyst. An exemplary rhodium catalyst is $[RhCl(CO)_2]_2$. The catalyst can be present in any amount that is less than a stoichiometric amount. For example, the catalyst can be present in an amount of from 0.01 mol % to about 50 mol %, 0.01 mol % to about 40 mol %, 0.01 mol % to about 30 mol %, 0.01 mol % to about 20 mol %, 0.01 mol % to about 10 mol %, 0.01 mol % to about 5 mol %, or 0.01 mol % to about 1 mol %. Preferably, about 1 mol % of the catalyst is utilized.

In preferred embodiments, the conversion of compounds of formula (II) to compounds of formula (I) are performed in an organic solvent. Exemplary organic solvents are hydrocarbon solvents, e.g., xylene, m-xylene; cyclic ethers, e.g., tetrahydrofuran; halogenated hydrocarbons, e.g., dichloromethane, and mixtures thereof.

The conversion of compounds of formula (II) to compounds of formula (I) can take place at temperatures ranging from ambient temperature to elevated temperature, for example, up to about 200° C. In some embodiments, the reaction is performed at about 20 to about 120° C. For example, the reaction can be performed at about 20, 25, 30, 35, 40, 45, 50, 55, 60, 65, 70, 75, 80, 85, 90, 95, 100, 105, 110, 115, or about 120° C.

In some embodiments, an oxide can be used in the conversion of compounds of formula (II) to compounds of formula (I). Oxides that can be used include, for example, N-oxides, sulfoxides, and mixtures thereof. An exemplary N-oxide is N-methyl-morpholine N-oxide. An exemplary sulfoxide is dimethylsulfoxide.

In some embodiments, the compounds of formula (I) are produced in a diastereomeric ratio of at least about 2:1, preferably at least about 3:1, more preferably at least about 4:1, more preferably at least about 5:1, and most preferably at least about 20:1.

Exemplary reaction conditions for converting compounds of formula (II) to compounds of formula (I) are set forth in Table 1.

TABLE 1

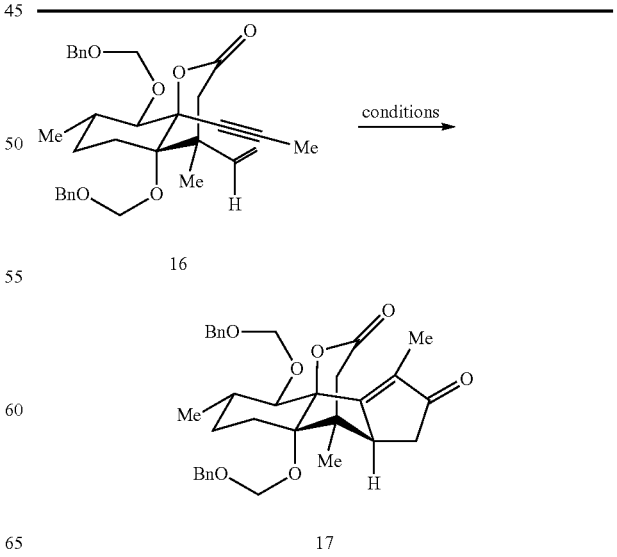

TABLE 1-continued

17'

| entry | conditions* | dr† | yield (%)‡ |
|---|---|---|---|
| 1 | Co$_2$(CO)$_8$(1.2 equiv), THF, 12 h; then DMSO, 65° C. | 2.2:1 | 46 |
| 2 | Co$_2$(CO)$_8$(1.2 equiv), CH$_2$Cl$_2$, 9 h; then NMO, 23° C. | 4.5:1 | 78 |
| 3 | Mo(CO)$_6$(1.2 equiv), DMSO, PhMe, 110° C. | — | trace |
| 4 | Mo(CO)$_3$(DMF)$_3$(1.1 equiv), CH$_2$Cl$_2$, 23° C. | >20:1 | 67 |
| 5 | [RhCl(CO)$_2$]$_2$(1 mol %), CO (1 atm), m-xylene, 110° C. | >20:1 | 85 |

*Reactions conducted on 0.2 mmol scale.
†Determined by $^1$H NMR spectroscopy.
‡Isolated yield after purification by silica gel chromatography.

In exemplary embodiments, the compound of formula (I) is compound 17 and the compound of formula (II) is compound 16.

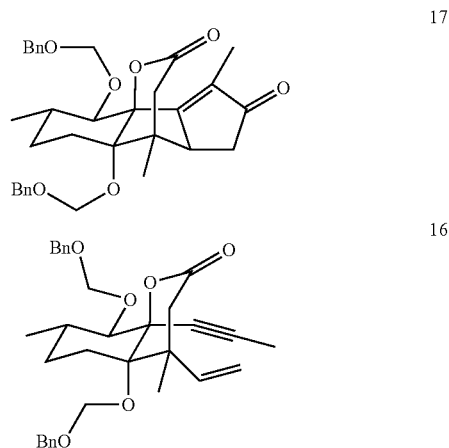

The compounds of formula (I) can be used as intermediates in the preparation of other compounds. For example, compounds of formula I can be used as intermediates in the sequences depicted in Scheme 1.

Scheme 1

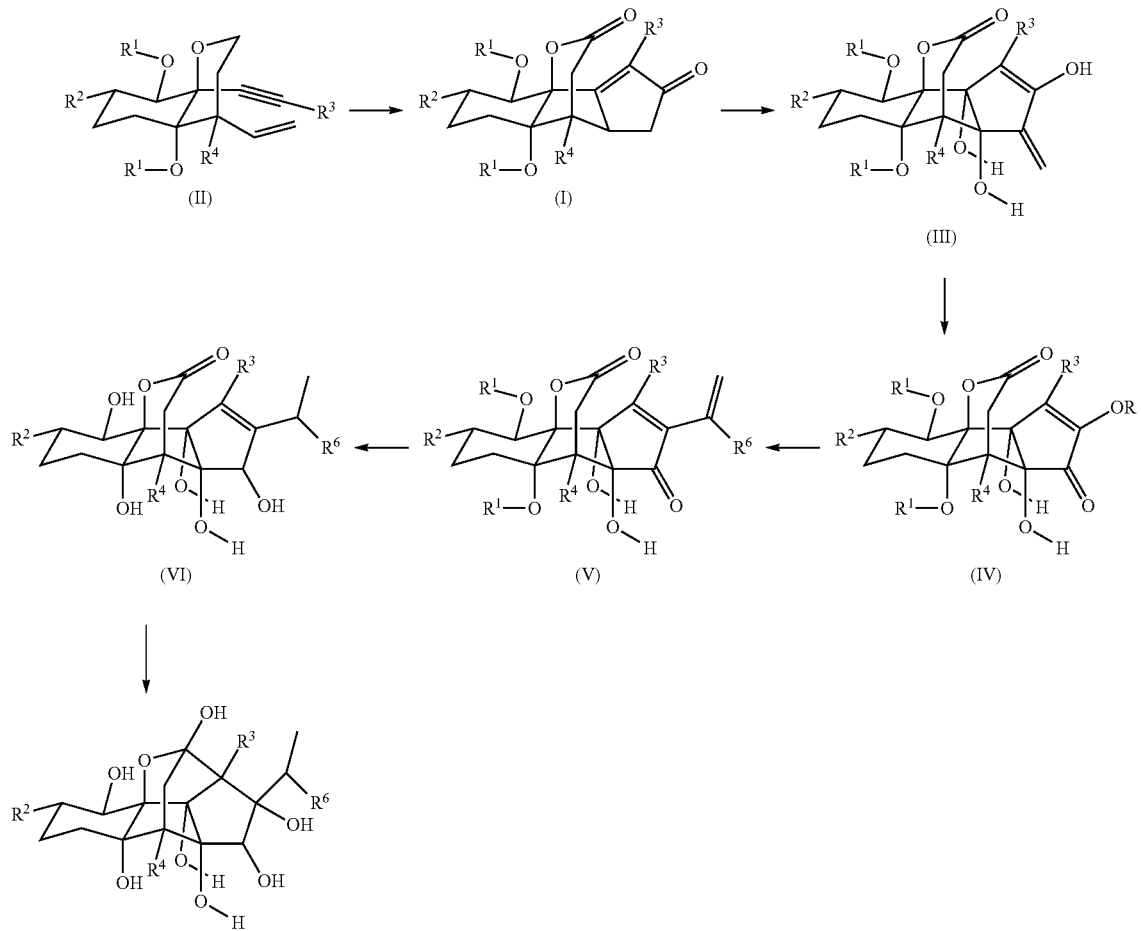

For example, according to the disclosure, compounds of formula (I) can be subjected to an oxidant, in an organic solvent, for a time and at a temperature sufficient to form compounds of formula (III).

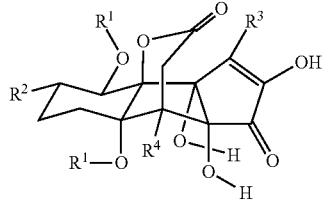

(III)

Preferably, the compound of formula (III) is compound 18.

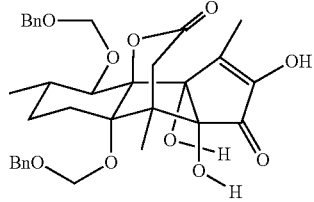

18

In some embodiments, the oxidant is selenium dioxide or molecular oxygen. In further embodiments, an excess, preferably about 5 to about 15 equivalents, and more preferably about 10 equivalents, of the oxidant is utilized. For example, about 5, 6, 7, 8, 9, 10, 11, 12, 13, 14, or 15 equivalents of the oxidant can be used.

Preferably, in preparing the compounds of formula (III), the organic solvent is anhydrous. In some embodiments, the organic solvent is a cyclic ether, e.g., dioxane. The preparation of compounds of formula (III) can be performed at any appropriate temperature, preferably elevated temperature, for example, at the reflux temperature of the organic solvent. In other embodiments, the reaction is performed at a temperature of about 90 to about 150° C., for example, about 90, 95, 100, 105, 110, 115, 120, 125, 130, 135, 140, 145, 150, 155, or about 160° C. A preferred temperature is about 110° C.

In other embodiments, compounds of formula (I) are subjected to the oxidant in the presence of a non-anhydrous organic solvent, i.e., the organic solvent includes water. In these embodiments, partial oxidation can occur to produce compounds of formula (IIIA):

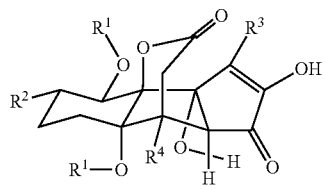

(IIIA)

An exemplary compound of formula (IIIA) is compound 21.

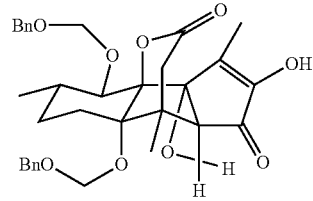

21

The compounds of formula (III) can be treated with a triflating agent, in an organic solvent, for a time and at a temperature sufficient to form compounds of formula (IV).

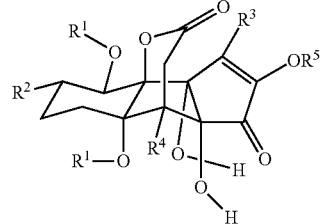

(IV)

wherein $R^5$ is —$SO_2$—$CF_3$ ("Tf").

Compound 19 is a preferred compound of formula (IV).

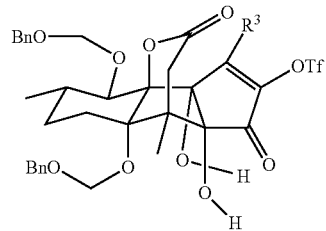

19

In some embodiments, the triflating agent is N-(5-chloro-2-pyridyl) bis(trifluoromethanesulfonimide), triflic anhydride, or N-phenyl-bis(trifluorosulfonimide). In further embodiments, the reaction is performed in the presence of an amine, preferably a trialkylamine such as trimethylamine, triethylamine, or diisopropylethylamine.

In some embodiments, the organic solvent used for the preparation of compounds of formula is a halogenated solvent such as, for example, dichloromethane. In still further embodiments, the reaction is performed at or below ambient temperature. Preferably, the conversion to compounds of formula (IV) takes place at low temperatures, preferably below about 0° C., for example, −10, −20, −30, −40, −50, −60, −70, or about −80 C. Preferably, the conversion of the compounds of formula (IV) takes place at about −80 to about 0° C., more preferably about −80 to about −70° C., and even more preferably about −78° C.

The compounds of formula (IV) can be converted to compounds of formula (V) by treating the compounds of formula (IV) with $R^6C(=CH_2)Sn(C_{1-6}alkyl)_3$ (wherein $R^6$ is $C_{1-6}alkyl$), in the presence of a catalyst, in an organic solvent, to provide compounds of formula (V). Such transformations are referred to in the art as "cross-coupling" reactions.

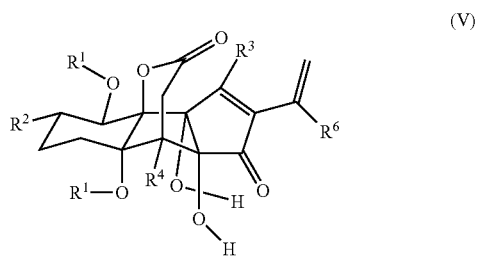

(V)

A preferred compound of formula (V) is compound 20, wherein R⁴ is methyl.

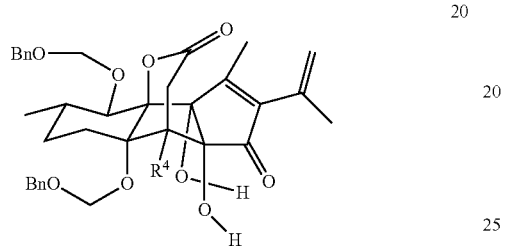

20

In some embodiments, $R^6C(=CH_2)Sn(C_{1-6}alkyl)_3$ is $CH_3C(=CH_2)SnBu_3$. According to the disclosure, about 2 to about 6 equivalents of the $R^6C(=CH_2)Sn(C_{1-6}alkyl)_3$ is used, for example, 1, 2, 3, 4, 5 or 6 equivalents with about 4 equivalents being particularly preferred.

The cross-coupling catalyst is a preferably a palladium catalyst, for example, $PdCl_2(PPh_3)_2$, Pd/C, $Pd(OAc)_2$, $Pd(PPh_3)_4$, and 1,1'-bis(diphenylphosphino) ferrocene)palladium(II) dichloride. The cross-coupling catalyst can be present in any amount that is less than a stoichiometric amount. For example, the catalyst can be present in an amount of from 0.01 mol % to about 90 mol %, 1 mol % to about 90 mol %, 5 mol % to about 90 mol %, 10 mol % to about 90 mol %, 20 mol % to about 90 mol %, 30 mol % to about 90 mol %, or 40 mol % to about 90 mol %. In further embodiments, about 20 to about 60 mol %, preferably about 40 mol %, of the catalyst is used.

In some embodiments, the cross-coupling reaction is performed in an organic solvent, preferably an ether, more preferably a cyclic ether, and even more preferably, a tetrahydrofuran such as methyl-tetrahydrofuran. In still other embodiments, the organic solvent is anhydrous.

In some embodiments, the reaction is performed at elevated temperatures, preferably about 80 to about 100° C., for example, about 80, 81, 82, 83, 84, 85, 86, 87, 88, 89, 90, 91, 92, 93, 94, 95, 96, 97, 98, 99, or 100° C., and more preferably about 90° C.

In come embodiments, the cross-coupling reaction is performed in the presence of an alkali salt, preferably an excess of the alkali salt, even more preferably lithium chloride. In certain embodiments, about 5 to about 15 equivalents, for example about 5, 6, 7, 8, 9, 10, 11, 12, 13, 14, or 15, preferably about 8 equivalents, of the alkali salt are utilized.

The compounds of formula (V) can be converted to compounds of formula (VI) via treatment with one or more reducing agents, and optionally a catalyst, for a time and at a temperature sufficient to provide the compounds of formula (VI).

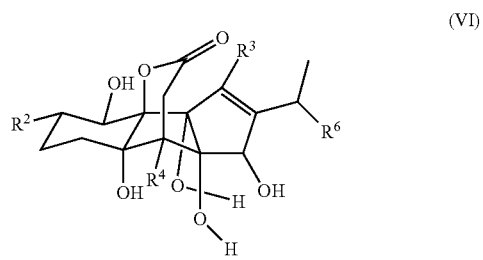

(VI)

Preferably, the compound of formula (VI) is compound 3.

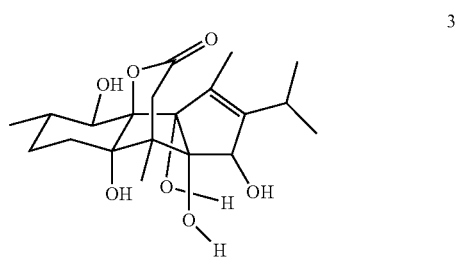 [SMILES: CC1=C(C(C)C)C(O)C2(O)C3(C)CC(=O)OC4(C(O)C(C)CCC34O)C12O]

3

In some embodiments, two reducing agents are used. Exemplary reducing agents include hydride, hydrogen, and a mixture thereof. In some embodiments, an excess of the reducing agent is utilized, preferably at least about 10 equivalents, more preferably about 10 to about 30 equivalents, for example about 10, 11, 12, 13, 14, 15, 16, 17, 18, 19, 20, 21, 22, 23, 24, 25, 26, 27, 28, 29, or 30 equivalents and most preferably about 20 equivalents.

In some aspects, the production of compounds of formula VI can use a first reducing agent and a second reducing agent.

In some embodiments, the first reducing agent is a hydride. Preferred hydrides include diisobutylaluminum hydride, lithium aluminum hydride, and lithium borohydride, with lithium borohydride being particularly preferred. In those aspects employing a hydride, the reaction can be performed in the presence of an organic solvent. For example, the organic solvent can be an ether, preferably a cyclic ether such as tetrahydrofuran. In those embodiments using hydride as a reducing agent, the process can be performed at reduced temperatures, preferably about −20 to about −10° C., for example, about −20, −19, −18, −17, −16, −15, −14, −13, −12, −11, or −10° C., more preferably about −15° C.

In some embodiments, the second reducing agent is hydrogen. In those embodiments employing hydrogen as a reducing agent, a hydrogenation catalyst is also used. Preferably, the hydrogenation catalyst is a palladium catalyst, for example, Pd/C, $Pd(OH)_2$/C, and the like. Alcoholic solvents, for example, methanol, ethanol, propanol, and mixtures thereof, are preferred solvents when the reducing agent is hydrogen.

A compound of formula (VI) can then be reacted with, for example, trifluoroperacetic acid to form an intermediate compound, i.e., an epoxide intermediate. In some embodiments, the epoxide intermediate is not isolated. In some embodiments, the trifluoroperacetic acid is prepared from trifluoroacetic anhydride and urea hydrogen peroxide. In other embodiments, the reaction is performed at low temperatures, preferably at or below ambient temperature. For example, the reaction is performed at less than about 20, 19, 18, 17, 16, 15, 14, 13, 12, 11, 10, 9, 8, 7, 6, 5, 4, 3, 2, 1 or 0° C., preferably about −5 to about 5° C., and more preferably about 0° C. In further embodiments, the reaction is performed using an organic solvent such as a halogenated hydrocarbon, preferably 1,2-dichloroethane. In yet other embodiments, the organic solvent is anhydrous. In further embodiments, the reaction is performed in the presence of an alkali phosphate, preferably a sodium phosphate, or more preferably disodium phosphate. An excess of the alkali phosphate may be used. In certain embodiments, at least about 2 equivalents, preferably about 2 to about 10 equivalents, for example, 2, 3, 4, 5, 6, 7, 8, 9, or 10 equivalents, of the alkali phosphate are utilized.

The epoxide intermediate is then subjected to reductive conditions to provide a compound of formula (VII). Exemplary reductive conditions for the preparation of compounds of formula (VII) are lithium metal in liquid ammonia. Preferably, the liquid ammonia is condensed from ammonia gas at reduced temperatures, preferably about −80 to about −70° C., and more preferably about −80° C. In some embodiments, the reaction is performed in an organic solvent, preferably an ether, more preferably a cyclic ether, and even more preferably tetrahydrofuran. In other embodiments, sodium metal is optionally added to the condensed ammonia prior to addition of the lithium metal.

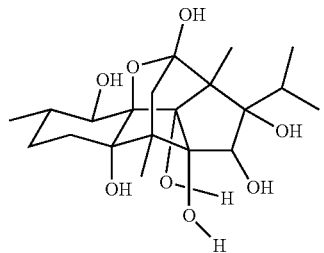

Preparation of the Compounds of Formula (II)

The compounds of formula (II) may be prepared using techniques known in the art. An exemplary sequence for the preparation of compounds of formula II is set forth in Scheme 2.

Scheme 2

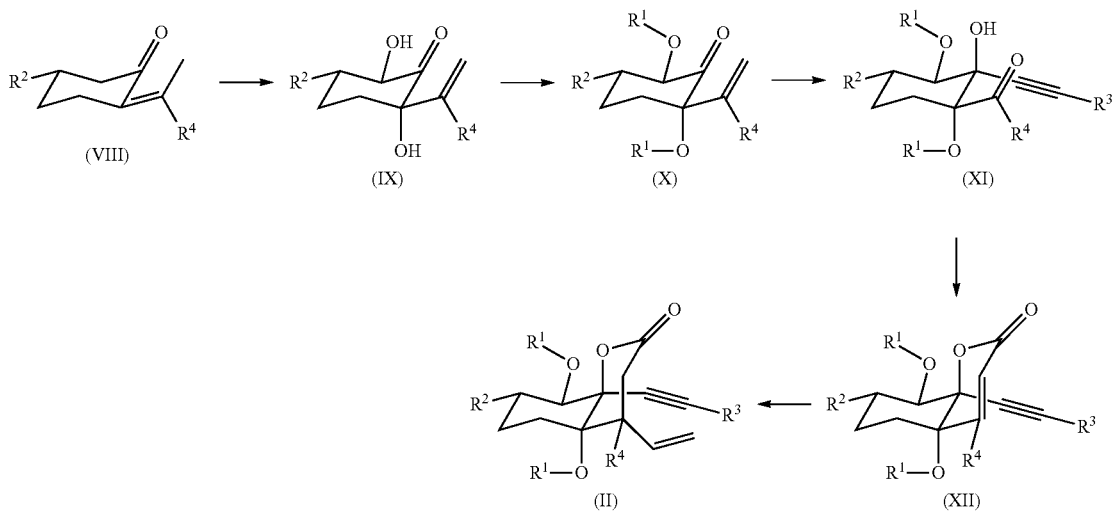

Referring to Scheme 2, compounds of formula (VIII) can be converted to compounds of formula (IX). In preferred aspects, the compounds of formula (IX) are prepared in high diastereomeric purity and are preferably prepared as single diastereomers. Compounds of formula (VIII) are known in the art or can be prepared from commercially available materials using methods known in the art. One exemplary compound of formula (VIII) is pulegone, preferably (S)-pulegone (10), wherein $R^2$ and $R^4$ are each methyl.

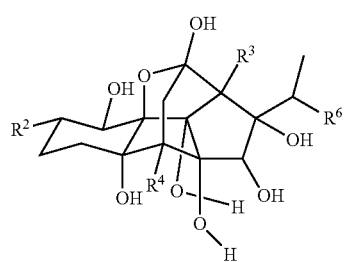

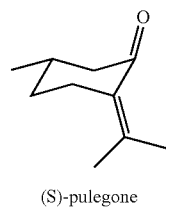

(S)-pulegone

In further embodiments, the compound of formula (VII) is compound 2. In yet other embodiments, the compound of formula (VII) is (+)-ryanodol.

Compounds of formula (VIII) can be treated with an oxidant, for example, an oxaziridine, in an organic solvent, in the presence of a base, for a time and at a temperature sufficient to produce a compound of formula IX. Preferred oxaziridine oxidants include, for example, rac-3-phenyl-2-(phenylsulfonyl)-1,2-oxaziridine and (7R,8aS)-9,9-dimethyltetrahydro-4H-4a,7-methanobenzo[c][1,2]oxarieno[2,3-b]isothiazole 3,3-dioxide. Preferably, an excess of the oxidant, that is, more than one equivalent of oxidant (e.g., 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or about 3.0 equivalents), is used. The organic solvent is preferably an ethereal solvent such as, for example, a cyclic ether such as tetrahydrofuran. Suitable bases include, for example, potassium hexamethyldisilazide and sodium hexamethyldisilazide. Preferably, an excess of the base, that is, more than one equivalent of base (e.g., 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or about 3.0), is used. Typically, the transformation to prepare compounds of formula (IX) is conducted at temperatures that are below ambient temperature, for example, between about −80° C. and about 15° C. The transformations can be conducted at, for example, about −80, −70, −60, −50, −40, −30, −20, −10, −5, 0, 5, 10, or about 15° C. In an exemplary transformation, a compound of formula (VIII) is treated with an excess of base (e.g., potassium hexamethyldisilazide), for example, about 2 to about 3 equivalents of base, in THF, at about −80° C., followed by the addition of an excess of the oxidant (e.g., an oxaziridine such as rac-3-phenyl-2-(phenylsulfonyl)-1,2-oxaziridine), for example, about 2 to about 3 equivalents of the oxidant, to provide the compound of formula (IX). An exemplary compound of formula (IX) is compound 12.

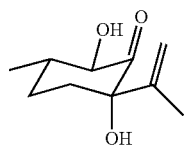

12

Referring to Scheme 2, compounds of formula (IX) can be converted to compounds of formula (X), wherein the two hydroxyl moieties are protected with reductively labile oxygen protecting groups or with acid labile oxygen protecting groups. Reductively labile oxygen protecting groups are known in the art and include, for example, benzyloxymethyl (BnO—CH₂—). See, e.g., Wuts and Greene, "Greene's Protective Groups in Organic Synthesis," Fourth Ed., John Wiley & Sons, Inc., 2007. Acid labile oxygen protecting groups are also known in the art and include, for example, trialkylsilylalkoxy methyl (e.g., trimethylsilylethoxy methyl ("SEM") and alkoxymethyl (e.g., methoxymethyl, "MOM"). See, e.g., Wuts and Greene, "Greene's Protective Groups in Organic Synthesis," Fourth Ed., John Wiley & Sons, Inc., 2007.

Compounds of formula (X) can be prepared using methods known in the art, for example, by treating a compound of formula (IX) with PG-LG, wherein PG is a reductively labile oxygen protecting group or an acid labile oxygen protecting group and LG is a leaving group, for example, a triflate or a halogen such as Cl. In preferred aspects, an excess of the PG-LG is used, for example, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 4.0, 5.0, 6.0, 7.0, 8.0, 9.0, or about 10.0 equivalents of PG-LG. The conversion of the compounds of formula (IX) to the compounds of formula (X) can be conducted in a suitable solvent, for example, a halogenated solvent such as methylene chloride. In exemplary embodiments, the transformation is conducted in the presence of a base, for example a trialkyl amine base such as diisopropylethylamine, triisopropylamine, or trimethylamine. In preferred aspects, an excess of the base is used, for example, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 4.0, 5.0, 6.0, 7.0, 8.0, 9.0, or about 10.0 equivalents of the base. The transformation to produce a compound of formula (X) can be conducted at a suitable temperature, for example, ambient temperature, elevated temperature, or reflux temperature, e.g., 20, 25 30, 35, 40, 45, 50, 55, 60, 65, 70, 75, 80, 85, 90, 95, or about 100° C., with 50° C. being particularly preferred. Halogen salts, for example iodide salts such as tetrabutylammonium iodide can also be used in the transformation to produce a compound of formula (X). Compound 13 is a preferred compound of formula (X).

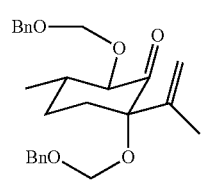

13

Referring to Scheme 2, compounds of formula (X) can be converted to compounds of formula (XI). For example, a compound of formula (X) can be converted to a compound of formula (XI-A) by treatment with a reagent such as R³—C≡C—MgBr (methods for preparation of which are known in the art), in an organic solvent, for a time and at a temperature sufficient to form a compound of formula (XI-A).

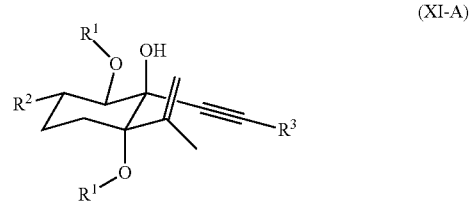

(XI-A)

Suitable solvents for the preparation of compounds of formula (XI-A) include ethereal solvents, in particular, cyclic ethers such as tetrahydrofuran. The transformations can take place at any suitable temperature, for example, ambient temperature or below. Suitable temperatures may include, for example, about 20, 15, 10, 5, 0, −5, −10, −15, −20, −25, −30, −40, −50, −60, −70 or about −80° C. Compounds of formula (XI-A) may be isolated. In other aspects, the compounds of formula (XI-A) are used without purification in further transformations. In preferred embodiments, the compounds of formula (XI-A) are prepared having a diastereomeric excess of at least about 2:1, preferably at least about 3:1, at least about 4:1, at least about 5:1, or at least about 6:1.

Compounds of formula (XI-A) can be converted to compounds of formula (XI) (see Scheme 2) by treatment with ozone (preferably O₃ and O₂ mixtures) followed by a phosphine such as PPh₃, in an organic solvent (or mixture of organic solvents), for a time and at a temperature sufficient to form the compounds of formula (XI). Suitable organic solvents include, for example, halogenated solvents such as methylene chloride, alcohols such as methanol, ethanol, and propanol, and mixtures thereof. Methylene chloride/methanol is one preferred solvent mixture. The preparation of compounds of formula (XI) is typically conducted at ambient or low temperature, for example, 20, 15, 10, 5, 0, −10, −20, −30, −40, −50, −60, −70, or −80° C., preferably about −80° C. Preferably, the compound of formula (XI) is compound 14.

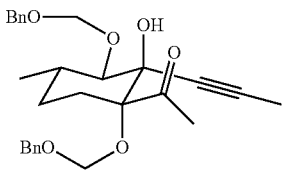

14

Referring to Scheme 2, compounds of formula (XI) can be converted to compounds of formula (XII-A).

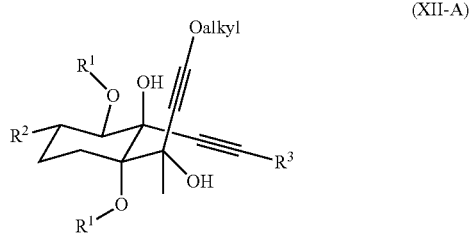

(XII-A)

For example, a compound of formula (XI) can be treated with an alkoxyethynylmagnesium bromide, e.g., ethoxyethynylmagnesium bromide or methoxyethynylmagnesium bromide. Preferably, an excess of the alkoxyethynylmagnesium bromide is used, for example, about 1.1, 1.5, 2, 3.5, 3, 3.5, 4, 4.5, 5, 5.5, 6, 6.5, 7, 7.5, 8, 8.5, 9, 9.5 or about 10, with about 5 equivalents being preferred. The reaction is performed in an organic solvent, preferably an ether, more preferably a cyclic ether, such as tetrahydrofuran. The preparation of a compound of formula (XII-A) can be performed at any appropriate temperature, for example ambient temperature. Low or elevated temperatures may also be appropriate. For example, compounds of formula (XII-A) can be prepared at about 20, 15, 10, or 0° C., or less. Alternatively, compounds of formula (XII-A) can be prepared at about 30, 40, 50, or 60° C., or more. Compounds of formula (XII-A) may be isolated. In other aspects, the compounds of formula (XII-A) are used without purification in further transformations.

Compounds of formula (XII-A) can be converted to compounds of formula (XII) (see Scheme 2). For example, a compound of formula (XII-A) can be treated with a cyclization/elimination catalyst, for example, a silver catalyst such as AgOTf or a gold catalyst, in an organic solvent, for a time and at a temperature sufficient to produce a compound of formula (XII). The catalyst can be present in an amount of from 0.01 mol % to about 50 mol %, 0.01 mol % to about 40 mol %, 0.01 mol % to about 30 mol %, 0.01 mol % to about 20 mol %, 0.01 mol % to about 10 mol %, 0.01 mol % to about 5 mol %, or 0.01 mol % to about 3 mol %. Preferably, about 2 mol % of the catalyst is used. Suitable solvents include hydrocarbon and aryl solvents, for example, toluene. The preparation of the compounds of formula (XII) can take place at ambient temperature or below, for example, about 25, 20, 15, 10, 5, 0, −5, −10, −15, or about −15° C. Compound 15, wherein $R^4$ is methyl, is a preferred compound of formula (XII):

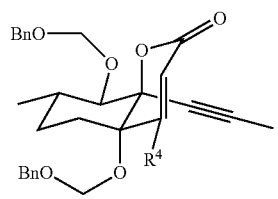

15

Compounds of formula (XII) can be converted to compounds of formula (II). (See Scheme 2). For example, a compound of formula (XII) can be treated with a magnesium divinyl cuprate reagent, in an organic solvent, for a time and at a temperature sufficient to produce a compound of formula (II). Magnesium divinyl cuprates are known in the art and may be purchased or prepared using known routes such as via combination of copper iodide and vinylmagnesium bromide. In those embodiments, about 1 to about 5 equivalents, for example, about 1, 2, 3, 4, or 5 equivalents, preferably about 3 equivalents, of a copper halide, preferably CuI, and about 1 to about 9 equivalents, for example, about 1, 2, 3, 4, 5, 6, 7, 8, or 9 equivalents, preferably about 6 equivalents of vinylmagnesium bromide are used. Suitable organic solvents include ethers, preferably cyclic ethers such as tetrahydrofuran. Compounds of formula (II) can be prepared ambient or low temperatures such as, e.g., about 25° C. or below about 0° C., preferably about −80 to about −20° C., for example, about −80, −75, −70, −65, −60, −55, −50, −45, −40, −35, −30, −25, or −20° C., or more preferably about −78 to about −30° C. In some aspects, the compounds of formula (II) are provided is a high diastereomeric ratio, for example, about 2:1, about 3:1, about 4:1, about 5:1, about 10:1, or as a single diastereomer.

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

EXAMPLES

Exemplary compounds useful in methods of the disclosure will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Unless otherwise stated, reactions were performed under an inert atmosphere (dry $N_2$ or Ar) with freshly dried solvents utilizing standard Schlenk techniques. Glassware was oven-dried at 120° C. for a minimum of four hours, or flame-dried utilizing a Bunsen burner under high vacuum. Tetrahydrofuran (THF), methylene chloride ($CH_2Cl_2$), 1,4-dioxane, and toluene (PhMe) were dried by passing through activated alumina columns. 2-Methyltetrahydrofuran (anhydrous, >99%, inhibitor-free) and m-xylene (anhydrous, >99%) were purchased from Sigma-Aldrich and stored under argon. Absolute ethanol (200 Proof) was purchased from Koptec. Methanol (HPLC grade) was purchased from Fisher Scientific. 1,2-Dichloroethane was purified via distillation over calcium hydride immediately before use. Anhydrous ammonia ($NH_3$) was purchased from Matheson Tri-Gas and distilled over sodium metal prior to use. Triethylamine ($Et_3N$) and N,N-diisopropylethylamine (i-$Pr_2NEt$) were distilled over calcium hydride prior to use. All reactions were monitored by thin-layer chromatography using EMD/Merck silica gel 60 F254 pre-coated plates (0.25 mm) and were visualized by UV (254 nm), p-anisaldehyde, or $KMnO_4$ staining. Flash column chromatography was performed using silica gel (SiliaFlash® P60, particle size 40-63 microns [230 to 400 mesh]) purchased from Silicycle. $^1H$ and $^{13}C$ NMR spectra were recorded on a Varian Inova 500 (at 500 MHz and 126 MHz, respectively) and are reported relative to internal $CHCl_3$ (1H, δ=7.26) or $CD_2HOD$ ($^1H$, δ=3.31), and $CDCl_3$ ($^{13}C$, δ=77.0), $CD_3OD$ ($^{13}C$, δ=49.0). Data for $^1H$ NMR spectra are reported as follows: chemical shift (δ ppm) (multiplicity, coupling constant (Hz), integration). Multiplicity and qualifier abbreviations are as follows: s=singlet, d=doublet, t=triplet, q=quartet, m=multiplet, br=broad, app=apparent. IR spectra were recorded on a Perkin Elmer Paragon 1000 spectrometer and are reported in frequency of absorption ($cm^{-1}$). HRMS were acquired using an Agilent 6200 Series TOF with an Agilent G1978A Multimode source in electrospray ionization (ESI), atmospheric pressure chemical ionization (APCI), or mixed (MM) ionization mode. Optical rotations were measured on a Jasco P-2000 polarimeter using a 100 mm path-length cell at 589 nm.

Reagents were purchased from commercial vendors or prepared as follows: Solid potassium hexamethyldisilazide (KHMDS, 95%) was purchased from Sigma-Aldrich and stored in a nitrogen-filled glovebox. Potassium hexamethyldisilazide solution (0.5 M in PhMe) was purchased from Sigma-Aldrich and stored under Argon. Rac-3-phenyl-2-(phenylsulfonyl)-1,2-oxaziridine (Davis Oxaziridine) was prepared according to literature procedures. See, e.g., Vishwakarma, Org. Synth. 66, 203-207 (1988). Chloromethyl benzyl ether ($BnOCH_2C_1$) was prepared from paraformaldehyde, benzyl alcohol, and gaseous hydrogen chloride according literature procedures. See, e.g., Hill, J. Am. Chem. Soc. 48, 257-262 (1926). Propynylmagnesium bromide (0.5 M in THF) was purchased from Alfa Aesar or freshly prepared via direct deprotonation of propyne with ethylmagnesium bromide (1 M in THF). Ethoxyacetylene (50 wt % in hexanes) was purchased from GFS Chemicals and used as received. Silver triflate (AgOTf, 99%), selenium dioxide ($SeO_2$, 99.8%), and chlorodicarbonyl rhodium (I) dimer ($[RhCl(CO)_2]_2$) were purchased from Strem Chemicals and stored in a nitrogen-filled glovebox. N-(5-Chloro-2-pyridyl) bis(trifluoromethanesulfonimide) (Comins Reagent) was purchased from Oakwood Chemicals. Copper(I) iodide (CuI) and palladium hydroxide on Carbon (Pearlman's Catalyst, 20 wt % on C) were purchased from Alfa Aesar. $LiBH_4$ (>95%) and lithium (wire stored in mineral oil, 99.9% trace metal basis) were purchased from Sigma-Aldrich.

Soda-lime (Flint) disposable culture tubes were purchased from Kimble Chase and used during silica gel chromatography for fraction collection in order to prevent formation of borate complexes formed with leached $B_2O_3$ from borosilicate (Pyrex) glassware. In some instances, leached $B_2O_3$ from use of borosilicate glass resulted in up to 10% of a stable borate. Treatment with aq. 3 M $KHF_2$ in MeOH followed by dilution with EtOAc and filtration over silica gel allowed for clean liberation of the reactive triol. The chloroform employed for silica gel chromatography contains 0.75% EtOH as a stabilizer.

Positional Numbering System.

The carbon numbering system and ring assignment as outlined by Deslongchamps was utilized for $^1H$ and $^{13}C$ NMR assignments. See, e.g., Belanger et al., Can. J. Chem. 57, 3348-3354 (1979); Deslongchamps et al., Can. J. Chem. 68, 115-126 (1990); Deslongchamps et al., Can. J. Chem. 68, 127-152 (1990); and Deslongchamps et al., Can. J. Chem. 68, 153-185 (1990). Assignments were performed with the aid of 2D $^1H$—$^1H$ (NOESY2D, gCOSY) and $^1H$—$^{13}C$ coupling experiments (gHSQC and gHMBC). See, Scheme 3.

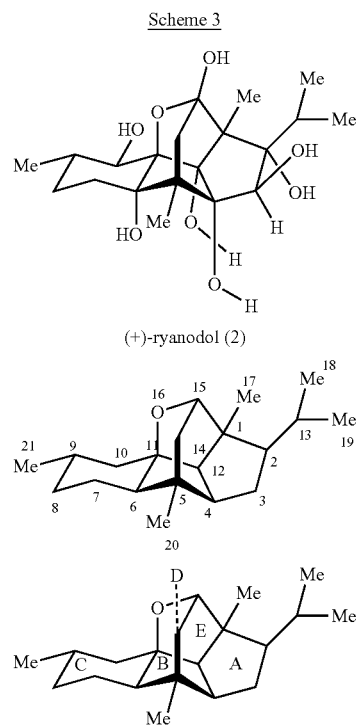

Scheme 3

Scheme 4 provides an exemplary synthesis of (+)-ryanodol from (S)-pulegone as provided in the following examples. The steps noted in this scheme are the following: 1. potassium hexamethyldisilazide (2.5 equiv), THF −78° C.; then 11 (2.4 equiv), 42-50% yield. 2. benzyl chloromethyl ether (5.0 equiv), $^iPr_2NEt$ (8.0 equiv), $^nBu_4NI$ (2.0 equiv), $CH_2Cl_2$, 50° C., 65% yield. 3. Propynylmagnesium bromide, THF, 0° C., 81% yield, 5:1 dr. 4. O$_3$/O$_2$, CH$_2$Cl$_2$/MeOH (4:1), −78° C.; then PPh$_3$, 91% yield. 5. Ethoxyethynylmagnesium bromide (5.0 equiv), THF, 0° C., 75% yield. 6. AgOTf (2 mol %), PhMe, 0° C., 90% yield. 7. CuI (3.0 equiv), vinylmagnesium bromide (6.0 equiv), THF, −78 to −30° C., 84% yield. 8. [RhCl(CO)$_2$]$_2$(1 mol %), CO (1 atm), m-xylene, 110° C., 85% yield. 9. SeO$_2$ (10 equiv), 4 Å MS, 1,4-dioxane, 110° C. 10. Comins' reagent, $^i$Pr$_2$NEt, CH$_2$Cl$_2$, −78 to 0° C., 28% yield, 2-steps. 11. PdCl$_2$(PPh$_3$)$_2$, tributyl(prop-1-en-2-yl)stannane, LiCl, 2-MeTHF, 85° C., 64% yield. 12. LiBH$_4$, THF, −15 to −10° C.; then KHF$_2$/MeOH. 13. H$_2$, Pd(OH)$_2$/C, EtOH, 61% yield, 2-steps. 14. Trifluoroacetic anhydride, urea hydrogen peroxide, Na$_2$HPO$_4$, 86% yield. 15. Li$^0$ wire, NH$_3$/THF, −78° C., 38% yield.

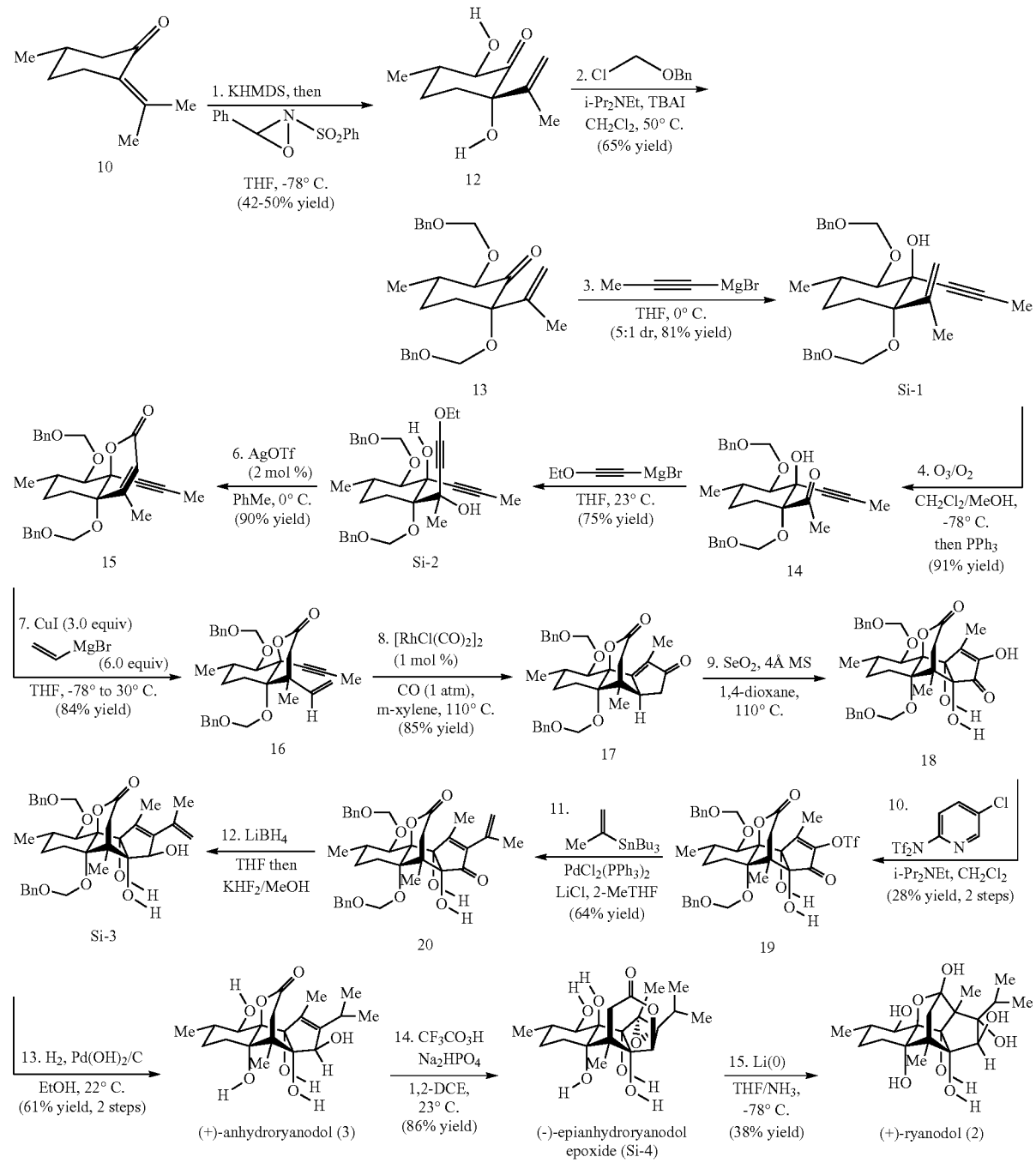

Example 1: Preparation of Diol 12

Both the selectivity and yields obtained for the α,α'-bishydroxylation of pulegone can depend on the quality of KHMDS and control of the temperature. Separation of the diastereomeric products was improved via use of wet silica gel, prepared as follows: Silica gel (SiliaFlash® P60, particle size 40-63 microns [230 to 400 mesh], purchased from Silicycle, 950 g) was slowly mixed with deionized water (50 mL) in a 1-liter media bottle. The silica was then vigorously shaken for five minutes, and then allowed to equilibrate for 12 h before use as normal for silica gel purification. The product obtained by this method was typically 97% pure by $^1$H NMR analysis, containing some minor oxaziridine-derived products.

Example 2: Preparation of Diol 12 (10 mmol Scale)

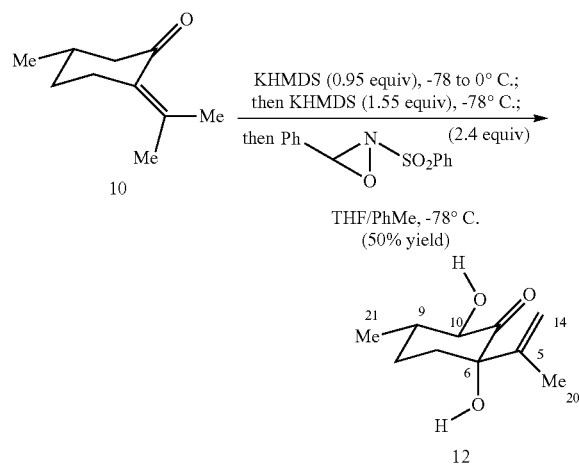

To a flame-dried, 250-mL, round-bottomed flask equipped with a magnetic stir bar was added (S)-pulegone (1.52 g, 10.0 mmol, 1.0 equiv) and THF (50 mL). The solution was cooled to −78° C. in a dry ice/acetone bath and KHMDS (19.0 mL, 0.5 M solution in PhMe, 9.50 mmol, 0.95 equiv) was added dropwise by cannula transfer over 10 minutes. After completion of the transfer, the dry ice/acetone bath was replaced with an ice/water bath, and the flask was stirred at 0° C. for 1 h. The solution was then recooled to −78° C. in a dry ice/acetone bath, and additional KHMDS solution (31.0 mL, 0.5 M solution PhMe, 15.5 mmol, 1.55 equiv) was added rapidly via cannula transfer and the flask stirred for 15 minutes to ensure complete cooling of the solution. A solution of rac-3-phenyl-2-(phenylsulfonyl)-1,2-oxaziridine (6.31 g, 24.0 mmol, 2.4 equiv) in THF (400 mL) was then added dropwise by cannula transfer over the course of 1 h, producing a deep orange-red solution that was stirred for 15 minutes. It is critical that the enolate solution is efficiently stirred during the addition to maintain a consistent internal temperature. Sat. aq. NH$_4$Cl (90 mL) was then added and the flask allowed to warm to ambient temperature and stirred for 1 h, until TLC-analysis indicated complete hydrolysis of the imine byproduct (N-benzylidenebenzenesulfonamide). The resulting mixture was extracted with EtOAc (150 mL), washed with sat. aq. NH$_4$Cl (2×150 mL), and the combined aqueous layers extracted with EtOAc (200 mL). The combined organic layers were washed with brine (200 mL), dried over anhydrous MgSO$_4$, filtered and concentrated in vacuo. Purification by silica gel chromatography (20 to 30 to 40% EtOAc in hexanes) on wet silica gel (see above) affords diol 12 as a white solid (923 mg, 5.01 mmol, 50% yield).

Example 3: Preparation of Diol 12 (120 mmol Scale)

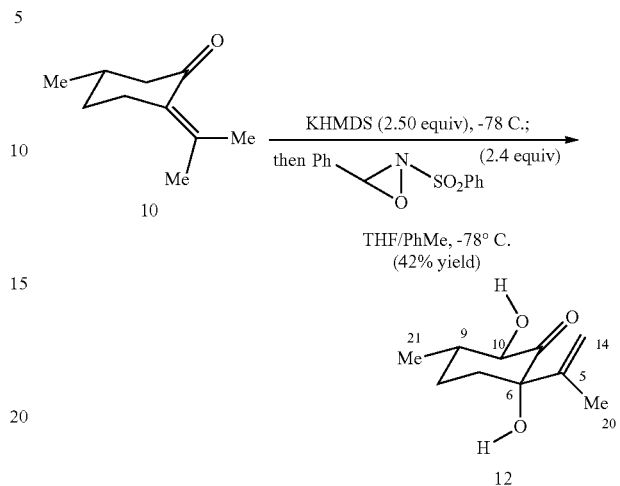

To a 1-liter, flame-dried flask equipped with a large magnetic stir bar was added solid KHMDS (95% KHMDS, 63.0 g, 300 mmol, 2.5 equiv) in a nitrogen-filled glovebox. The flask was capped with a rubber septum, removed from the glovebox, and anhydrous THF (300 mL) was charged to the flask and the resulting mixture stirred at 22° C. for 10 minutes to ensure complete dissolution of the solid. The resulting solution was then cooled to −78° C. in a dry ice/acetone bath—a large capacity Pope brand cryogenic dewar was utilized for this procedure. After stirring for 20 minutes at −78° C., a solution of (S)-pulegone (18.3 g, 120 mmol, 1.0 equiv) in THF (50 mL) was added dropwise by cannula transfer over 30 minutes, resulting in a homogenous yellow solution that was stirred for an additional 20 minutes. A solution of rac-3-phenyl-2-(phenylsulfonyl)-1,2-oxaziridine (72.1 g, 276 mmol, 2.3 equiv) in THF (400 mL) was then added dropwise by cannula transfer over the course of 1 h, producing a deep orange-red solution that was stirred for an additional 15 minutes. The reaction was then quenched by the addition of sat. aq. NH$_4$Cl solution (250 mL) and the cold bath replaced with a water bath at ambient temperature. Once the temperature of the mixture had reached 23° C., the biphasic mixture was then stirred rapidly for 1 h to allow for hydrolysis of the imine byproduct (N-benzylidenebenzenesulfonamide). The mixture was subsequently poured into a separatory funnel, diluted with EtOAc (500 mL), and washed with sat. aq. NH$_4$Cl (3×250 mL). The combined aqueous washings were then extracted with EtOAc (2×300 mL), and the combined organic layers washed with brine (500 mL), dried over anhydrous MgSO$_4$, filtered, and concentrated in vacuo. The resulting thick slurry was then redissolved in EtOAc (100 mL) and treated with hexanes (400 mL), resulting in the precipitation of benzenesulfonamide, and the solids removed by filtration over Celite, rinsing with 4:1 hexanes/EtOAc (200 mL) to fully elute off the products. Concentration in vacuo affords an orange oil. Repeated purification by silica gel chromatography (500 g wet silica, 20 to 30 to 40% EtOAc in hexanes) affords a thick, slightly yellow oil that was determined to be 97% pure by $^1$H NMR (9.19 g, 49.9 mmol, 42% yield).

Residual imine byproduct, N-benzylidenebenzenesulfonamide, has a slightly higher $R_f$ than the product that can be challenging to remove by chromatography. In cases where the imine is not fully hydrolyzed, the product can be redissolved in EtOAc (200 mL) and stirred with sat. aq. NH$_4$Cl (200 mL) for 12 h. The resulting benzaldehyde and benzenesulfonamide products are then readily removed by silica gel chromatography.

A $^1$H NMR spectrum is included of the material obtained through the above procedures (97% purity). A sample was further purified by silica gel chromatography for characterization purposes.

TLC (40% EtOAc/Hexanes), R$_f$: 0.43 (p-anisaldehyde); $^1$H NMR (CDCl$_3$, 500 MHz): δ 5.06 (m, 2H, C=CH$_2$), 4.34 (dd, J=10.9, 4.7 Hz, 1H, HC$_{10}$), 3.37 (d, J=4.7 Hz, 1H, OH), 2.48 (s, 1H, OH), 2.03-1.82 (m, 3H, H$_2$C$_7$, H$_A$C$_8$), 1.81 (app. s, 3H, H$_3$C$_{20}$), 1.68-1.52 (m, 2H, H$_B$C$_8$, HC$_9$), 1.19 (d, J=6.3 Hz, C$_{21}$H$_3$); $^{13}$C NMR (CDCl$_3$, 126 MHz): δ 209.7 (C$_{11}$=O), 145.4 (C$_5$), 112.5 (C$_{14}$H$_2$), 80.1 (C$_6$), 77.8 (C$_{10}$H), 43.6 (C$_9$H), 37.1 (C$_7$H$_2$), 26.7 (C$_8$H$_2$), 19.7 (C$_{20}$H$_3$), 19.0 (C$_{21}$H$_3$); FTIR (NaCl, thin film): 3421, 2955, 2929, 1720, 1456, 1376 cm$^{-1}$; LRMS: calc'd for [M+H]$^+$: 185.1, found: 185.1; [α]$_D^{25}$: −38 (c=1.0 CHCl$_3$).

Example 4: Preparation of Ketone 13

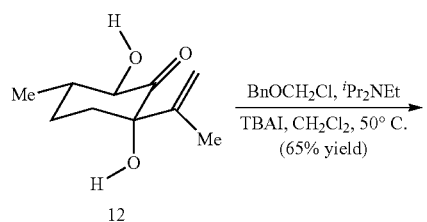

12

To a 500-mL, flame-dried flask was added diol 12 (9.14 g, 49.6 mmol, 1.0 equiv), tetrabutylammonium iodide (36.6 g, 99.2 mmol, 2.0 equiv), and anhydrous CH$_2$Cl$_2$ (200 mL). The solution was cooled to 0° C. in an ice/water bath and $^i$Pr$_2$NEt (69 mL, 400 mmol, 8.0 equiv) was added rapidly via syringe. After 10 minutes, chloromethyl benzyl ether (34.4 mL, 248 mmol, 5.0 equiv) was added dropwise via syringe. The cold bath was subsequently removed and the solution was allowed to warm to 20° C. over 45 minutes. The flask was equipped with an oven-dried reflux condenser and then submerged into a preheated oil bath at 55° C. (internal temp. 50° C.), resulting in gentle reflux of the pale yellow solution. As the reaction proceeds, the color of the solution changes to a deep red. After 40 h, the solution was cooled to ambient temperature, poured into a 1-liter separatory funnel, diluted with additional CH$_2$Cl$_2$ (250 mL), and washed sequentially with sat. aq. NaHCO$_3$ (250 mL) and sat. aq. NH$_4$Cl (3×200 mL). The combined aqueous washings were then extracted with CH$_2$Cl$_2$ (2×100 mL), then the combined organic layers were washed with 0.2 N NaOH (300 mL) and brine (300 mL), dried over anhydrous MgSO$_4$, filtered, and concentrated in vacuo to afford a thick red slurry. EtOAc (100 mL) was added and the suspension vigorously agitated to ensure suspension of the solids. The suspension was then treated with hexanes (400 mL) resulting in the additional precipitation of ammonium salts, and the solids removed via filtration over Celite, rinsing with hexanes/EtOAc (4:1, 200 mL). Concentration in vacuo resulted in isolation of a homogeneous red oil. Purification by silica gel chromatography (7 to 9 to 12% EtOAc in hexanes) afforded ketone 13 as a thick, colorless oil (13.6 g, 32.1 mmol, 65% yield).

A similar yield was obtained albeit at longer reaction times in the absence of Bu$_4$NI.

TLC (10% EtOAc/Hexanes), R$_f$: 0.23 (UV, p-anisaldehyde). $^1$H NMR (500 MHz, CDCl$_3$): δ 7.38-7.26 (m, 10H, H—Ar), 5.20 (app. p, J=1.4 Hz, 1H, H$_A$C$_{14}$), 5.05 (app. t, J=1.0 Hz, 1H, H$_B$C$_{14}$), 4.84 (d, J=7.1 Hz, 1H, BnOCH$_2$O), 4.80 (d, J=11.9 Hz, 1H, PhCH$_2$O), 4.78 (d, J=7.1 Hz, 1H, BnOCH$_2$O), 4.78 (d, J=7.1 Hz, 1H, BnOCH$_2$O), 4.74 (d, J=11.7 Hz, 1H, PhCH$_2$O), 4.72 (d, J=7.1 Hz, 1H, BnOCH$_2$O), 4.66 (d, J=11.7 Hz, 1H, PhCH$_2$O), 4.65 (d, J=10.9 Hz, 1H, HC$_{10}$), 4.64 (d, J=11.9 Hz, 1H, PhCH$_2$O), 2.29 (dt, J=14.4, 2.9 Hz, 1H, H$_A$C$_7$), 1.96-1.77 (m, 3H, H$_A$C$_8$, H$_B$C$_7$, HC$_9$), 1.74-1.67 (m, 1H, H$_B$C$_8$), 1.71 (app. q, J=0.7 Hz, 3H, H$_3$C$_{20}$), 1.20 (d, J=6.1 Hz, 3H, H$_3$C$_{21}$). $^{13}$C NMR (126 MHz, CDCl$_3$): δ 206.3 (C$_{11}$=O), 142.8 (C$_5$), 137.8 (C$_{Ar-ipso}$), 137.5 (C$_{Ar-ipso}$), 128.5 (C$_{Ar}$H), 128.4 (C$_{Ar}$H), 127.9 (C$_{Ar}$H), 127.8 (C$_{Ar}$H), 127.8 (C$_{Ar}$H), 127.6 (C$_{Ar}$H), 116.4 (C$_{14}$H$_2$), 94.3 (BnOCH$_2$O), 90.4 (BnOCH$_2$O), 87.8 (C$_6$), 83.0 (C$_{10}$H), 71.1 (PhCH$_2$O), 69.9 (PhCH$_2$O), 41.8 (C$_9$H), 34.2 (C$_7$H$_2$), 27.6 (C$_8$H$_2$), 19.7 (C$_{20}$H$_3$), 19.5 (C$_{21}$H$_3$). FTIR (NaCl, thin film): 2890, 1734, 1454, 1379, 1157, 1057, 1015 cm$^{-1}$; HRMS: calc'd for [M+Na]$^+$: 447.2142, found: 447.2126. [α]$_D^{25}$: +58 (c=1.0, CHCl$_3$).

Example 5: Preparation of Enyne SI-1

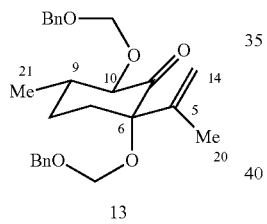

13

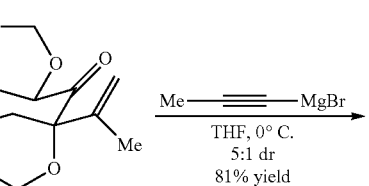

13

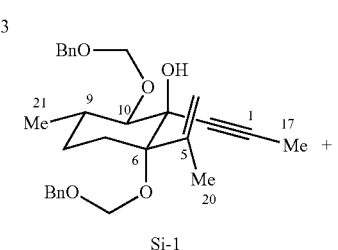

Si-1

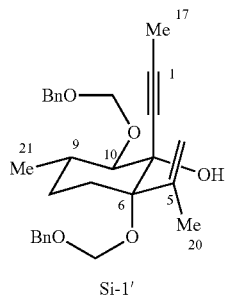

Si-1'

To a 1-liter, flame-dried round-bottomed flask was charged ketone 13 (13.3 g, 31.3 mmol, 1.0 equiv) and THF (310 mL). The solution was placed in an ice/water bath at 0° C. and stirred for 25 minutes for adequate cooling, then a solution of propynylmagnesium bromide (0.5 M solution, 125 mL, 62.5 mmol, 2.0 equiv) was added dropwise by cannula transfer over 45 min. The reaction was stirred for an additional 30 min and then carefully quenched by the addition of sat. aq. NH$_4$Cl (300 mL). The mixture was diluted with Et$_2$O (300 mL) and washed with sat. aq. NH$_4$Cl (2×100 mL), then the combined aqueous layers extracted with Et$_2$O (200 mL). The combined organic layers were then washed with brine (300 mL), dried over anhydrous MgSO$_4$, filtered, and concentrated in vacuo to afford a thick, light yellow oil. $^1$H NMR analysis of the crude product indicated that the reaction occurs with complete consumption of starting material in a 5:1 diastereomeric ratio. Purification by silica gel chromatography (15 to 20 EtOAc in hexanes) afforded enyne SI-1 as a viscous oil that slowly solidifies into colorless, semicrystalline needles (11.8 g, 25.4 mmol, 81% yield) in addition to minor diastereomer SI-1' (1.75 g, 3.76 mmol, 12% yield).

Major Diastereomer (SI-1):

TLC (20% EtOAc/Hexanes), R$_f$: 0.38 (p-anisaldehyde); $^1$H NMR (500 MHz, CDCl$_3$): δ 7.40-7.33 (m, 8H, H—Ar), 7.32-7.27 (m, 2H, H—Ar), 5.24 (p, J=1.5 Hz, 1H, H$_A$C$_{14}$), 5.20 (d, J=6.9 Hz, 1H, BnOCH$_2$O), 5.20 (dd, J=1.8, 0.8 Hz, 1H, H$_B$C$_{14}$), 4.96 (d, J=6.8 Hz, 1H, BnOCH$_2$O), 4.89 (d, J=12.0 Hz, 1H, PhCH$_2$O), 4.82 (d, J=11.8 Hz, 1H, PhCH$_2$O), 4.77 (d, J=6.8 Hz, 1H, BnOCH$_2$O), 4.74 (d, J=6.8 Hz, 1H, BnOCH$_2$O), 4.63 (d, J=12.0 Hz, 1H, PhCH$_2$O), 4.58 (d, J=11.8 Hz, 1H, PhCH$_2$O), 3.64 (d, J=10.6 Hz, 1H, HC$_{10}$), 2.72 (s, 1H, OH), 2.17-2.08 (m, 1H, H$_A$C$_7$), 1.96-1.92 (m, 1H, HC$_9$), 1.81 (s, 3H, H$_3$C$_{17}$), 1.74 (dt, J=14.4, 3.1 Hz, 1H, H$_B$C$_7$), 1.55-1.48 (m, 2H, H$_2$C$_8$), 1.09 (d, J=6.5 Hz, 3H, H$_3$C$_{21}$); $^{13}$C NMR (126 MHz, CDCl$_3$): δ 144.7 (C$_5$), 138.0 (C$_{Ar-ipso}$), 137.9 (C$_{Ar-ipso}$), 128.4 (C$_{Ar}$H), 128.4 (C$_{Ar}$H), 127.8 (C$_{Ar}$H), 127.7 (C$_{Ar}$H), 127.6 (C$_{Ar}$H), 117.0 (C$_{14}$H$_2$), 96.7 (BnOCH$_2$O), 90.3 (BnOCH$_2$O), 86.4 (C$_{10}$H), 85.3 (C$_{12}$), 82.0 (C), 80.9 (C), 75.3 (C$_1$), 70.7 (PhCH$_2$O), 70.5 (PhCH$_2$O), 31.8 (C$_9$H), 27.6 (C$_8$H$_2$), 27.1 (C$_7$H$_2$), 22.0 (C$_{20}$H$_3$), 19.0 (C$_{21}$H$_3$), 3.8 (C$_{17}$H$_3$); FTIR (NaCl, thin film): 3401, 2952, 2927, 2240, 1497, 1453, 1379, 1022 cm$^{-1}$; HRMS: calc'd for [M+Na]$^+$: 487.2445, found: 487.2438; [α]$_D^{25}$: +84 (c=1.1, CHCl$_3$).

Minor Diastereomer (SI-1'):

TLC (20% EtOAc/Hexanes), R$_f$: 0.31 (p-anisaldehyde); $^1$H NMR (500 MHz, CDCl$_3$): δ 7.39-7.31 (m, 8H, H—Ar), 7.31-7.26 (m, 2H, H—Ar), 5.24 (p, J=1.4 Hz, 1H, H$_A$C$_{14}$), 5.16 (dd, J=1.6, 0.8 Hz, 1H, H$_B$C$_{14}$), 5.10 (d, J=7.0 Hz, 1H, BnOCH$_2$O), 4.86 (d, J=7.0 Hz, 1H, BnOCH$_2$O), 4.85 (d, J=12.0 Hz, 1H, PhCH$_2$O), 4.81 (d, J=11.8 Hz, 1H, PhCH$_2$O), 4.81 (d, J=7.2 Hz, 1H, BnOCH$_2$O), 4.77 (d, J=7.2 Hz, 1H, BnOCH$_2$O), 4.70 (d, J=12.0 Hz, 1H, PhCH$_2$O), 4.55 (d, J=11.9 Hz, 1H, PhCH$_2$O), 4.05 (s, 1H, OH), 3.58 (d, J=10.5 Hz, 1H, HC$_{10}$), 2.19-2.11 (m, 1H, H$_A$C$_7$), 1.96 (q, J=0.7 Hz, 3H, H$_3$C$_{20}$), 1.95-1.87 (m, 2H, H$_B$C$_7$, HC$_9$), 1.87 (s, 3H, H$_3$C$_{17}$), 1.59-1.54 (m, 2H, H$_2$C$_8$), 1.06 (d, J=6.5 Hz, 3H, H$_3$C$_{21}$); $^{13}$C NMR (126 MHz, CDCl$_3$): δ 144.5 (C$_5$), 137.8 (C$_{Ar-ipso}$), 137.5 (C$_{Ar-ipso}$), 128.4 (C$_{Ar}$H), 128.4 (C$_{Ar}$H), 127.8 (C$_{Ar}$H), 127.8 (C$_{Ar}$H), 127.7 (C$_{Ar}$H), 127.7 (C$_{Ar}$H), 117.5 (C$_{14}$H$_2$), 97.0 (BnOCH$_2$O), 91.1 (BnOCH$_2$O), 89.2 (C$_{10}$H), 86.4 (C$_{12}$), 83.2 (C$_6$), 78.3 (C$_{11}$), 77.5 (C$_1$), 71.1 (PhCH$_2$O), 70.2 (PhCH$_2$O), 35.3 (C$_9$H), 29.9 (C$_7$H$_2$), 27.9 (C$_8$H$_2$), 22.4 (C$_{20}$H$_3$), 18.6 (C$_{21}$H$_3$), 3.9 (C$_{17}$H$_3$); FTIR 487.2445, found: 487.2456; [α]$_D^{25}$: +61 (c=0.90, CHCl$_3$).

Example 6: Preparation of Methyl Ketone 14

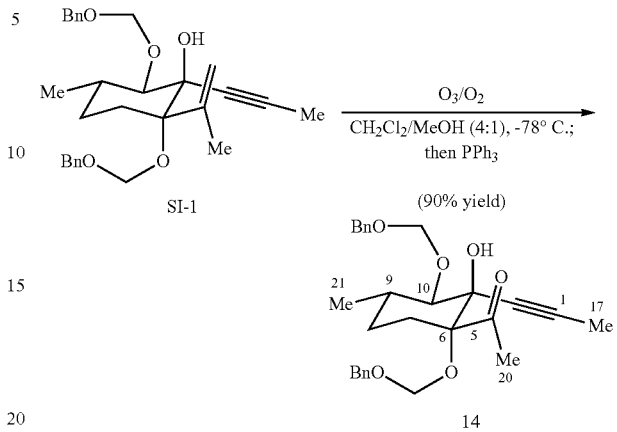

To a 1-liter, round-bottomed flask was charged enyne SI-1 (11.7 g, 25.2 mmol, 1.0 equiv), followed by CH$_2$Cl$_2$ (400 mL) and MeOH (100 mL). The solution was purged with O$_2$ by means of a gas dispersion tube while cooling to −78° C. in a dry ice/acetone bath. A mixture of O$_3$/O$_2$ was then passed through the solution and the reaction carefully monitored by TLC to track disappearance of the starting material. After 4.5 h, the solution slowly changed from a colorless solution to a very slight, pale blue color. O$_2$ (g) was sparged through the solution at an increased rate to purge out excess ozone, followed by N$_2$ (g) for 10 minutes. Triphenylphosphine (6.61 g, 25.2 mmol, 1.0 equiv) was then added in a single portion to the mixture at −78° C. The mixture was allowed to warm to 23° C. with efficient stirring under N$_2$ over the course of 1 h, then concentrated in vacuo to afford a thick oil. Purification by silica gel chromatography (20 to 30 to 35% EtOAc in hexanes, sample loaded in 10 mL of CH$_2$Cl$_2$) afforded methyl ketone 14 as a white amorphous solid (10.6 g, 22.7 mmol, 90% yield).

TLC (40% EtOAc/Hexanes), R$_f$: 0.50 (UV, p-anisaldehyde); $^1$H NMR (500 MHz, CDCl$_3$): δ 7.38-7.33 (m, 8H, H—Ar), 7.33-7.27 (m, 2H, H—Ar), 5.17 (d, J=7.0 Hz, 1H, BnOCH$_2$O), 4.93 (d, J=7.0 Hz, 1H, BnOCH$_2$O), 4.89 (d, J=6.8 Hz, 1H, BnOCH$_2$O), 4.88 (d, J=11.9 Hz, 1H, PhCH$_2$O), 4.77 (d, J=11.9 Hz, 1H, PhCH$_2$O), 4.76 (d, J=6.8 Hz, 1H, BnOCH$_2$O), 4.64 (d, J=11.9 Hz, 1H, PhCH$_2$O), 4.62 (d, J=11.9 Hz, 1H, PhCH$_2$O), 3.57 (d, J=10.6 Hz, 1H, HC$_{10}$), 3.08 (s, 1H, OH), 2.40 (s, 3H, H$_3$C$_{20}$), 2.26 (ddd, J=15.0, 13.8, 4.3 Hz, 1H, H$_A$C$_7$), 1.96-1.85 (m, 1H, HC$_9$), 1.83 (s, 3H, H$_3$C$_{17}$), 1.77 (dt, J=15.0, 3.2 Hz, 1H, H$_B$C$_7$), 1.57 (dtd, J=13.6, 4.3, 2.9 Hz, 1H, H$_A$C$_8$), 1.36 (tdd, J=13.7, 12.5, 3.5 Hz, 1H, H$_B$C$_8$), 1.06 (d, J=6.5 Hz, 3H, H$_3$C$_{21}$); $^{13}$C NMR (126 MHz, CDCl$_3$): δ 209.4 (C$_5$=O), 137.8 (C$_{Ar-ipso}$), 137.4 (C$_{Ar-ipso}$), 128.4 (C$_{Ar}$H), 128.4 (C$_{Ar}$H), 127.8 (C$_{Ar}$H), 127.7 (C$_{Ar}$H), 127.7 (C$_{Ar}$H), 127.7 (C$_{Ar}$H), 96.5 (BnOCH$_2$O), 91.1 (BnOCH$_2$O), 88.1 (C), 85.7 (C$_{10}$H), 82.9 (C), 80.1 (C), 72.5 (C$_1$), 70.8 (PhCH$_2$O), 70.6 (PhCH$_2$O), 31.5 (C$_9$H), 28.1 (C$_{20}$H$_3$), 27.1 (CH$_2$), 24.6 (CH$_2$), 18.7 (C$_{21}$H$_3$), 3.8 (C$_{17}$H$_3$); FTIR (NaCl, thin film): 3402, 2951, 2927, 2235, 1713, 1453, 1020 cm$^{-1}$; HRMS: calc'd for [M+Na]$^+$: 489.2248, found: 489.2246; [α]$_D^{25}$: +97 (c=1.0, CHCl$_3$).

Example 7: Preparation of Diyne SI-2

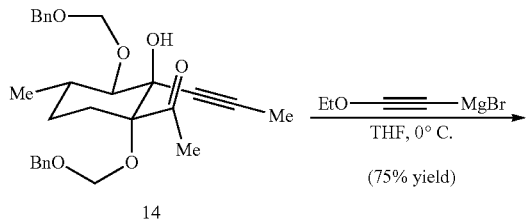

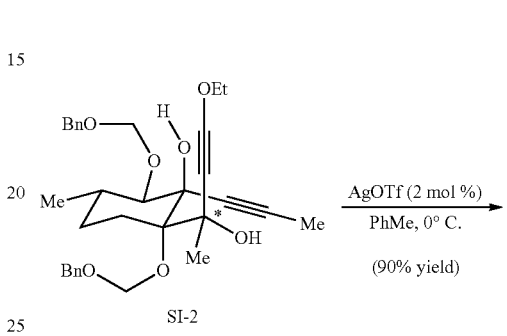

*stereochemistry unassigned

To a 1-liter, oven-dried, round-bottomed flask was added ethylmagnesium bromide (1.0 M in THF, 114 mL, 114 mmol, 5.0 equiv) and THF (114 mL). The solution was cooled to 0° C. in an ice/water bath and ethoxyacetylene (50 wt % in hexanes, 23.8 mL, 6.0 equiv) added dropwise by syringe. The resulting brown solution was stirred at 0° C. for 15 minutes, then removed from the ice bath and allowed to warm to room temperature over 30 minutes. The dark brown solution was then recooled to 0° C. in an ice/water bath, and a solution of ketone 14 (10.6 g, 22.7 mmol, 1.0 equiv) in THF (100 mL) was added via cannula transfer over 30 minutes. Upon completion of the addition, the dark brown solution was stirred for an additional 20 minutes, then quenched by the addition of sat. aq. NH$_4$Cl (300 mL), diluted with EtOAc (300 mL), and washed with additional sat. aq. NH$_4$Cl (2×200 mL). The combined organic layers were extracted with additional EtOAc (250 mL), and the combined organic layers were washed with brine (300 mL), dried over anhydrous MgSO$_4$, filtered, and concentrated in vacuo. $^1$H NMR analysis of the mixture reveals approximately 85% conversion. Purification of the resulting brown oil, twice, by silica gel chromatography (30 to 35% EtOAc in hexanes) afforded diyne SI-2 (9.13 g, 17.0 mmol, 75% yield) as a light yellow oil that very slowly solidified to a slightly yellow amorphous solid under high vacuum, along with a mixture of recovered starting material and product (2.2 g) that could be resubjected for further material throughput.

TLC (40% EtOAc/Hexanes), R$_f$: 0.40 (UV, p-anisaldehyde); $^1$H NMR (500 MHz, CDCl$_3$): δ 7.40-7.27 (m, 10H, H—Ar), 5.13 (d, J=6.9 Hz, 1H, BnOCH$_2$O), 5.11 (d, J=6.8 Hz, 1H, BnOCH$_2$O), 4.99 (d, J=6.8 Hz, 1H, BnOCH$_2$O), 4.95 (d, J=6.9 Hz, 1H, BnOCH$_2$O), 4.88 (d, J=11.9 Hz, 1H, PhCH$_2$O), 4.81 (d, J=11.7 Hz, 1H, PhCH$_2$O), 4.74 (d, J=11.6 Hz, 1H, PhCH$_2$O), 4.60 (d, J=11.9 Hz, 1H, PhCH$_2$O), 4.50 (s, 1H, OH), 4.03 (q, J=7.1 Hz, 2H, OCH$_2$CH$_3$), 3.70 (s, 1H, OH), 3.56 (d, J=10.6 Hz, 1H, HC$_{10}$), 2.27 (dt, J=15.6, 3.4 Hz, 1H, H$_A$C$_7$), 2.12 (ddd, J=15.4, 13.8, 4.3 Hz, 1H, H$_B$C$_7$), 1.88-1.81 (m, 1H, HC$_9$), 1.84 (s, 3H, H$_3$C$_{17}$), 1.80 (s, 3H, H$_3$C$_{20}$), 1.55 (dq, J=11.8, 4.1 Hz, 1H, H$_A$C$_8$), 1.35-1.25 (m, 1H, H$_B$C$_8$), 1.31 (t, J=7.1 Hz, 3H, OCH$_2$CH$_3$), 1.03 (d, J=6.5 Hz, 3H, H$_3$C$_{21}$); $^{13}$C NMR (126 MHz, CDCl$_3$): δ 137.9 (C$_{Ar\text{-}ipso}$), 137.7 (C$_{Ar\text{-}ipso}$), 128.4 (C$_{Ar}$H), 128.3 (C$_{Ar}$H), 128.0 (C$_{Ar}$H), 127.7 (C$_{Ar}$H), 127.6 (C$_{Ar}$H), 127.6 (C$_{Ar}$H), 97.0 (BnOCH$_2$O), 94.4 (C$_{15}$), 89.2 (BnOCH$_2$O), 87.5 (C$_{10}$H), 84.1 (C$_6$), 83.3 (C$_{12}$), 81.7 (C$_{11}$), 75.4 (C$_1$), 74.8 (C$_5$), 74.2 (OCH$_2$CH$_3$), 70.6 (PhCH$_2$O), 70.2 (PhCH$_2$O), 42.5 (C$_{14}$), 31.6 (C$_9$H), 28.9 (C$_{20}$H$_3$), 27.0 (C$_8$H$_2$), 22.8 (C$_7$H$_2$), 18.7 (C$_{21}$H$_3$), 14.5 (OCH$_2$CH$_3$), 3.9 (C$_{17}$H$_3$); FTIR (NaCl, thin film): 3402, 2983, 2929, 2262, 1457, 1022 cm$^{-1}$; HRMS: calc'd for [M+Na]$^+$: 559.2666, found: 559.2662; [α]$_D^{25}$: +11 (c=1.1, CHCl$_3$).

Example 8: Preparation of Lactone 15

To a 200 mL, round-bottomed flask was added diyne SI-2 (8.97 g, 16.7 mmol, 1.0 equiv) and anhydrous PhMe (84 mL). The solution was stirred vigorously at 23° C. for 15 minutes to ensure complete dissolution of the starting material, then the flask was submerged in an ice/water bath and allowed to cool over 15 minutes. AgOTf (85.6 mg, 0.334 mmol, 0.02 equiv) was weighed into a 1-dram vial in a nitrogen-filled glovebox and then added directly to the solution against a positive pressure of Argon, and the resulting mixture stirred vigorously at 0° C. for 20 min. The entire cold solution was then directly and rapidly loaded onto a silica gel column pre-equilibrated with 20% EtOAc in hexanes, and the compound purified by silica gel chromatography (20 to 30 to 40% EtOAc in hexanes) to provide lactone 15 as a pale yellow oil (7.38 g, 15.0 mmol, 90% yield).

TLC (40% EtOAc/Hexanes), R$_f$: 0.40 (UV, p-anisaldehyde); $^1$H NMR (500 MHz, CDCl$_3$): δ 7.39-7.27 (m, 10H, H—Ar), 5.85 (q, J=1.5 Hz, 1H, HC$_{14}$), 5.12 (d, J=7.3 Hz, 1H, BnOCH$_2$O), 5.08 (d, J=6.6 Hz, 1H, BnOCH$_2$O), 5.06 (d, J=6.6 Hz, 1H, BnOCH$_2$O), 4.91 (d, J=7.3 Hz, 1H, BnOCH$_2$O), 4.84 (d, J=11.9 Hz, 1H, PhCH$_2$O), 4.76 (d, J=11.7 Hz, 1H, PhCH$_2$O), 4.65 (d, J=11.7 Hz, 1H, PhCH$_2$O), 4.59 (d, J=12.0 Hz, 1H, PhCH$_2$O), 3.70 (d, J=10.1 Hz, 1H, HC$_{10}$), 2.07 (m, HC$_9$), 2.01 (d, J=1.5 Hz, 3H, H$_3$C$_{20}$), 2.02-1.96 (m, 1H H$_A$C$_7$), 1.77 (s, 3H, H$_3$C$_{17}$), 1.71-1.47 (m, 3H, H$_B$C$_7$, H$_2$C$_8$), 1.12 (d, J=6.6 Hz, 3H, H$_3$C$_{21}$); $^{13}$C NMR (126 MHz, CDCl$_3$): δ 162.5 (C$_{15}$=O), 160.9 (br s, C$_5$) 138.1 (C$_{Ar\text{-}ipso}$), 137.4 (C$_{Ar\text{-}ipso}$), 128.5 (C$_{Ar}$H), 128.4 (C$_{Ar}$H), 127.9 (C$_{Ar}$H), 127.8 (C$_{Ar}$H), 127.7 (C$_{Ar}$H), 127.5 (C$_{Ar}$H), 118.6 (C$_{14}$H), 96.8 (BnOCH$_2$O), 91.5 (BnOCH$_2$O), 85.2 (C$_{12}$), 83.8 (C$_{10}$H), 81.4 (C$_{11}$), 80.6 (C$_6$), 76.6 ($C_1$), 70.6 (PhCH$_2$O), 70.5 (PhCH$_2$O), 32.4 ($C_9$H), 32.3 ($C_7H_2$), 27.2 ($C_8H_2$), 18.5 ($C_{21}H_3$), 17.9 ($C_{20}H_3$), 3.8 ($C_{17}H_3$); FTIR (NaCl, thin film): 2954, 2927, 2245, 1727, 1247, 1167, 1025 cm$^{-1}$; HRMS: calc'd for [M+Na]$^+$: 513.2248, found: 513.2236; $[\alpha]_D^{25}$: +34 (c=0.50, CHCl$_3$).

Example 9: Preparation of Enyne 16

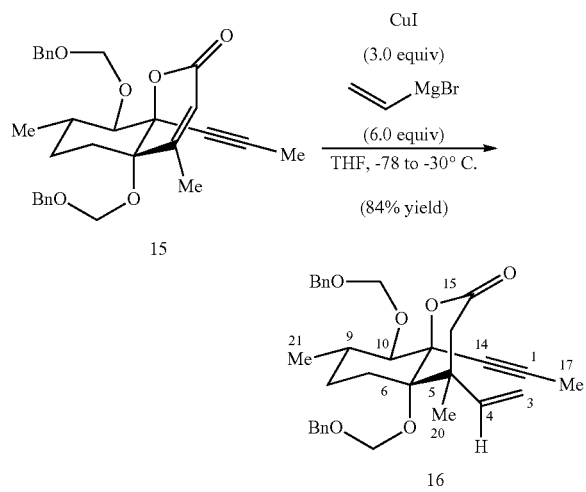

To a flame-dried, 1-liter, round-bottomed flask was charged CuI (8.46 g, 44.4 mmol, 3.0 equiv) and THF (400 mL). The suspension was cooled to −78° C. in a dry ice/acetone bath and vinylmagnesium bromide (1 M in THF, 89 mL, 89 mmol, 6.0 equiv) was added dropwise by syringe. Upon completion of the addition, the mixture was stirred for an additional 15 minutes, then a solution of lactone 15 (7.26 g, 14.8 mmol, 1.0 equiv) in THF (100 mL) was added dropwise by cannula transfer. The resulting mixture was maintained at −78° C. for 15 minutes, then the mixture was gradually warmed to −30° C. over 30 minutes, and stirring maintained at −30° C. for 30 minutes. The reaction was then carefully quenched by the addition of sat. aq. NH$_4$Cl (300 mL) and warmed to ambient temperature. The reaction was then diluted with Et$_2$O (400 mL) and the biphasic mixture filtered through a short pad of Celite to remove precipitated red copper solids. The resulting mixture was then poured into a separatory funnel and washed with sat. aq. NH$_4$Cl (2×200 mL), and the combined aqueous layers extracted with additional Et$_2$O (2×200 mL). The combined organic layers were then washed with brine (400 mL), dried over anhydrous MgSO$_4$ and filtered over a short pad of silica gel to remove additional red copper-based precipitates, and the resultant solution concentrated in vacuo to afford a colorless oil. Purification of the crude residue by silica gel chromatography (20 to 30% EtOAc in hexanes) afforded enyne 16 as a slightly yellow oil (6.45 g, 12.4 mmol, 84% yield).

TLC (40% EtOAc/Hexanes), R$_f$: 0.53 (UV, p-anisaldehyde); $^1$H NMR (500 MHz, CDCl$_3$): δ 7.39-7.27 (m, 10H, H—Ar), 6.81 (dd, J=17.7, 10.8 Hz, 1H, HC$_4$), 5.16 (d, J=7.2 Hz, 1H, BnOCH$_2$O), 5.09 (dd, J=4.0, 0.8 Hz, 1H), 5.08 (dd, J=17.7, 0.8 Hz, 1H, H$_A$C$_3$), 5.08 (dd, J=10.8, 0.8 Hz, 1H, H$_B$C$_3$), 4.99 (d, J=7.2 Hz, 1H, BnOCH$_2$O), 4.89 (d, J=11.9 Hz, 1H, PhCH$_2$O), 4.82 (d, J=7.1 Hz, 1H, BnOCH$_2$O), 4.77 (d, J=11.7 Hz, 1H, PhCH$_2$O), 4.71 (d, J=7.1 Hz, 1H, BnOCH$_2$O), 4.60 (d, J=11.9 Hz, 1H, PhCH$_2$O), 4.51 (d, J=11.8 Hz, 1H, PhCH$_2$O), 3.66 (d, J=10.7 Hz, 1H, HC$_{10}$), 3.49 (d, J=15.6 Hz, 1H, H$_A$C$_{14}$), 2.13 (d, J=15.6 Hz, 1H, H$_B$C$_{14}$), 2.07-1.94 (m, 2H, HC$_9$, H$_A$C$_7$), 1.91 (s, 3H, H$_3$C$_{17}$), 1.56-1.46 (m, 3H, H$_B$C$_7$, H$_2$C$_8$), 1.26 (s, 3H, H$_3$C$_{20}$), 1.08 (d, J=6.5 Hz, 3H, H$_3$C$_{21}$); $^{13}$C NMR (126 MHz, CDCl$_3$): δ 170.6 (C$_{15}$=O), 144.9 (C$_4$H), 138.0 (C$_{Ar\text{-}ipso}$), 137.4 (C$_{Ar\text{-}ipso}$), 128.4 (C$_{Ar}$H), 128.4 (C$_{Ar}$H), 127.8 (C$_{Ar}$H), 127.8 (C$_{Ar}$H), 127.8 (C$_{Ar}$H), 127.6 (C$_{Ar}$H), 111.6 (C$_3$H$_2$), 97.6 (BnOCH$_2$O), 90.5 (BnOCH$_2$O), 86.0 (C$_{10}$H), 85.8 (C$_{12}$), 83.3 (C$_6$), 81.3 (C$_{11}$), 77.2 (C$_1$), 71.0 (PhCH$_2$O), 70.5 (PhCH$_2$O), 44.2 (C$_{14}$H$_2$), 43.7 (C$_5$), 31.0 (C$_9$H), 27.4 (C$_8$H$_2$), 26.7 (C$_7$H$_2$), 24.1 (C$_{20}$H$_3$), 18.8 (C$_{21}$H$_3$), 3.9 (C$_{17}$H$_3$); FTIR (NaCl, thin film): 2954, 2928, 2871, 1752, 1454, 1237, 1026 cm$^{-1}$; HRMS: calc'd for [M+Na]$^+$: 541.2561, found: 541.2539; $[\alpha]_D^{25}$: +76 (c=1.0, CHCl$_3$).

A sample of the minor diastereomer (17') was obtained via purification of entry 2 for characterization purposes.

Minor Diastereomer (17'):

TLC (70% EtOAc/Hexanes), R$_f$: 0.52 (UV, p-anisaldehyde). $^1$H NMR (500 MHz, CDCl$_3$): δ 7.38-7.26 (m, 8H, H—Ar), 7.25-7.20 (m, 2H, H—Ar), 5.24 (d, J=5.9 Hz, 1H, BnOCH$_2$O), 5.06 (d, J=6.0 Hz, 1H, BnOCH$_2$O), 4.83 (d, J=6.8 Hz, 1H, BnOCH$_2$O), 4.77 (d, J=11.8 Hz, 1H, PhCH$_2$O), 4.70 (d, J=6.8 Hz, 1H, BnOCH$_2$O), 4.64 (d, J=11.8 Hz, 1H, PhCH$_2$O), 4.47 (d, J=11.5 Hz, 1H, PhCH$_2$O), 4.41 (d, J=11.5 Hz, 1H, PhCH$_2$O), 4.02 (d, J=11.0 Hz, 1H, HC$_{10}$), 2.83 (dddd, J=6.7, 5.1, 2.4, 1.0 Hz, 1H, HC$_4$), 2.69 (dd, J=18.6, 1.0 Hz, 1H, H$_A$C$_{14}$), 2.65 (dd, J=16.4, 6.7 Hz, 1H, H$_A$C$_3$), 2.63 (d, J=18.7 Hz, 1H, H$_B$C$_{14}$), 2.35-2.23 (m, 1H, HC$_9$), 2.33 (dd, J=16.4, 5.1 Hz, 1H, H$_B$C$_3$), 2.08 (d, J=2.4 Hz, 3H, H$_3$C$_{17}$), 2.02-1.91 (m, 1H, H$_A$C$_7$), 1.79-1.64 (m, 2H, H$_B$C$_7$, H$_A$C$_8$), 1.63-1.52 (m, 1H, H$_B$C$_8$), 1.19 (d, J=6.5 Hz, 3H, H$_3$C$_{21}$), 1.11 (s, 3H, H$_3$C$_{20}$); $^{13}$C NMR (126 MHz, CDCl$_3$): δ 208.8 (C$_2$=O), 172.3 (C$_{15}$=O), 168.0 (C$_{12}$), 137.9 (C$_{Ar\text{-}ipso}$), 136.4 (C$_{Ar\text{-}ipso}$), 135.9 (C$_1$), 128.6 (C$_{Ar}$H), 128.3 (C$_{Ar}$H), 128.2 (C$_{Ar}$H), 128.1 (C$_{Ar}$H), 127.7 (C$_{Ar}$H), 127.6 (C$_{Ar}$H), 91.8 (BnOCH$_2$O), 90.6 (C), 89.3 (BnOCH$_2$O), 89.0 (C), 78.2 (C$_{10}$H), 70.5 (PhCH$_2$O), 70.5 (PhCH$_2$O), 51.1 (C$_4$H), 48.0 (C$_{14}$H$_2$), 42.8 (C$_5$), 41.8 (C$_3$H$_2$), 30.0 (C$_9$H), 28.7 (C$_8$H$_2$), 21.9 (C$_7$H$_2$), 18.5 (C$_{21}$H$_3$), 16.7 (C$_{20}$H$_3$), 9.4 (C$_{17}$H$_3$); FTIR (NaCl, thin film): 2929, 1748, 1707, 1453, 1234, 1025, 1008 cm$^{-1}$; HRMS: calc'd for [M+Na]$^+$: 569.2510, found: 569.2510; $[\alpha]_D^{25}$: −140 (c=0.20, CHCl$_3$).

Example 10: Preparation of Enone 17

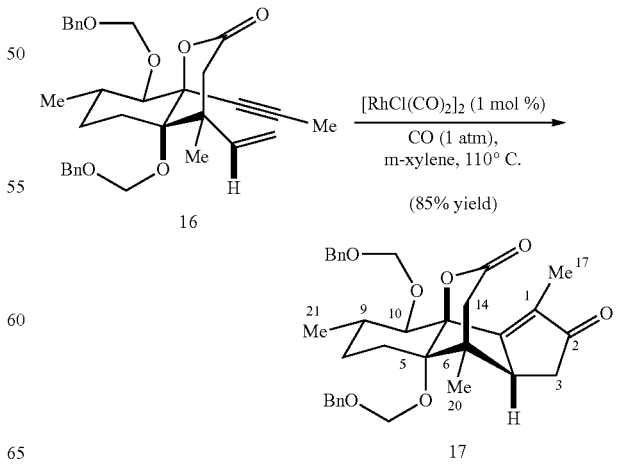

To a 500-mL, round-bottomed flask containing enyne 16 (6.33 g, 12.2 mmol, 1.0 equiv) was added [RhCl(CO)$_2$]$_2$ (47.4 mg, 0.122 mmol, 0.01 equiv) in a nitrogen-filled glovebox. The flask was capped with a rubber septum, removed from the glovebox, and anhydrous m-xylene (120 mL) was added via syringe. The flask was equipped with an outlet needle and dry argon was bubbled through the solution for five minutes, followed by carbon monoxide for five minutes. The vent needle was removed and a CO atmosphere was maintained in the flask by means of a double-walled balloon, then the flask was submerged into a preheated oil bath at 110° C. After heating for 2 h, the reaction was cooled to ambient temperature, sparged with N$_2$ to thoroughly expel excess CO gas, then the solvent was removed in vacuo (an efficient rotovap was utilized with a bath temperature at 50° C.) to afford a thick, dark orange oil. $^1$H NMR analysis of the unpurified reaction mixture could not identify traces of the undesired diastereomer, 17'. Purification by silica gel chromatography (30 to 50 to 70% EtOAc in hexanes) afforded enone 17 as a crunchy foam. Dissolution of the resulting foam in Et$_2$O followed by reevaporation (2×100 mL) affords enone 17 as an off-white powder (5.66 g, 10.4 mmol, 85% yield). Single crystals suitable for X-ray diffraction were obtained from this material by crystallization from Et$_2$O.

TLC (70% EtOAc/Hexanes), $R_f$: 0.60 (UV, p-anisaldehyde); $^1$H NMR (500 MHz, CDCl$_3$): δ 7.37-7.27 (m, 10H, H—Ar), 5.02 (d, J=6.9 Hz, 1H, BnOCH$_2$O), 4.98 (d, J=6.9 Hz, 1H, BnOCH$_2$O), 4.85 (d, J=11.9 Hz, 1H, PhCH$_2$O), 4.85 (d, J=6.7 Hz, 1H, BnOCH$_2$O), 4.78 (d, J=6.8 Hz, 1H, BnOCH$_2$O), 4.70 (d, J=11.7 Hz, 1H, PhCH$_2$O), 4.63 (d, J=11.7 Hz, 1H, PhCH$_2$O), 4.59 (d, J=11.9 Hz, 1H, PhCH$_2$O), 4.13 (d, J=10.4 Hz, 1H, HC$_{10}$), 3.63 (dddd, J=6.6, 3.3, 2.7, 1.3 Hz, 1H, HC$_4$), 2.48 (dd, J=18.4, 6.6 Hz, 1H, H$_A$C$_3$), 2.32 (dd, J=19.5, 1.3 Hz, 1H, H$_B$C$_{14}$), 2.28-2.21 (m, 1H, HC$_9$), 2.25 (d, J=19.6 Hz, 1H, H$_A$C$_{14}$), 2.06 (dd, J=18.4, 3.3 Hz, 1H, H$_B$C$_3$), 2.03-1.96 (m, 1H, H$_A$C$_7$), 1.93 (d, J=2.7 Hz, 3H, H$_3$C$_{17}$), 1.75 (dtd, J=11.5, 4.3, 2.6 Hz, 1H, H$_A$C$_8$), 1.71-1.57 (m, 2H, H$_B$C$_7$, H$_B$C$_7$), 1.16 (d, J=6.6 Hz, 3H, H$_3$C$_{21}$), 1.14 (s, 3H, H$_3$C$_{20}$); $^{13}$C NMR (126 MHz, CDCl$_3$): δ 209.2 (C$_2$=O), 174.1 (C$_{15}$=O), 168.8 (C$_{12}$), 140.9 (C$_1$), 137.6 (C$_{Ar-ipso}$), 137.0 (C$_{Ar-ipso}$), 128.5 (C$_{Ar}$H), 128.4 (C$_{Ar}$H), 128.0 (C$_{Ar}$H), 127.9 (C$_{Ar}$H), 127.7 (C$_{Ar}$H), 127.6 (C$_{Ar}$H), 95.5 (BnOCH$_2$O), 90.1 (BnOCH$_2$O), 89.3 (C$_6$), 87.1 (C$_{11}$), 79.2 (C$_{10}$H), 71.2 (PhCH$_2$O), 70.7 (PhCH$_2$O), 51.0 (C$_4$H), 45.4 (C$_5$), 37.3 (C$_{14}$H$_2$), 35.6 (C$_3$H$_2$), 32.1 (C$_9$H), 28.5 (C$_8$H$_2$), 20.6 (C$_7$H$_2$), 18.8 (C$_{21}$H$_3$), 18.2 (C$_{20}$H$_3$), 10.1 (C$_{17}$H$_3$); FTIR (NaCl, thin film): 2954, 2872, 1748, 1707, 1454, 1209, 1154, 1042, 1025 cm$^{-1}$; HRMS: calc'd for [M+Na]$^+$: 569.2510, found: 569.2523; [α]$_D^{25}$: +180 (c=1.0, CHCl$_3$).

Example 11: Preparation of Diosphenol 21

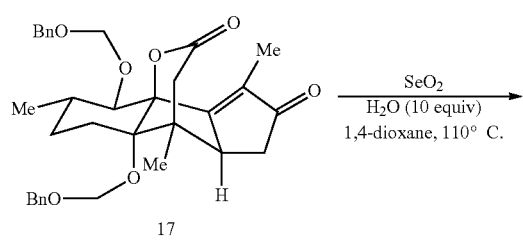

17

To a 2-dram vial was added enone 17 (109.0 mg, 0.200 mmol, 1.0 equiv), SeO$_2$ (222 mg, 20.0 mmol, 10 equiv), dioxane (4.0 mL), and H$_2$O (36 μL, 2.00 mmol, 10 equiv). The vial was sealed with a Teflon cap, then submerged in an oil bath preheated to 110° C. for 1 h. The vial was then cooled to ambient temperature, diluted with EtOAc (50 mL) and washed with sat. aq. NaHCO$_3$ (2×50 mL). The combined aqueous layers were then extracted with EtOAc (15 mL), the combined organics dried over anhydrous Na$_2$SO$_4$, and the solution filtered and concentrated in vacuo to afford a dark orange foam. Purification by silica gel chromatography (2% MeOH in CH$_2$Cl$_2$) affords an orange foam that was used in the subsequent reaction without additional purification.

A sample of diosphenol 21 was further purified by repeated chromatography to remove Se-based byproducts to afford an analytically pure sample for characterization purposes, affording 21 as a colorless foam.

TLC (70% EtOAc/Hexanes), $R_f$: 0.50 (UV, KMnO$_4$); $^1$H NMR (500 MHz, CDCl$_3$): δ 7.40-7.27 (m, 10H, H—Ar), 5.39 (s, 1H, HOC$_2$), 5.09 (d, J=5.4 Hz, 1H, BnOCH$_2$O), 5.01 (d, J=6.8 Hz, 1H, BnOCH$_2$O), 4.97 (d, J=6.8 Hz, 1H), 4.84 (d, J=5.4 Hz, 1H, BnOC$_2$O), 4.76 (d, J=11.7 Hz, 1H, PhCH$_2$O), 4.71 (d, J=11.7 Hz, 1H, PhCH$_2$O), 4.71 (d, J=12.2 Hz, 1H, PhCH$_2$O), 4.64 (d, J=12.2 Hz, 1H, PhCH$_2$O), 4.55 (s, 1H, OH), 3.99 (d, J=10.5 Hz, 1H, HC$_{10}$), 2.92 (s, 1H, HC$_4$), 2.29 (dd, J=19.9, 1.2 Hz, 1H, H$_B$C$_{14}$), 2.24 (d, J=19.9 Hz, 1H, H$_A$C$_{14}$), 2.11-2.03 (m, 1H, HC$_9$), 2.10 (s, 3H, H$_3$C$_{17}$), 1.96-1.88 (m, 1H, H$_A$C$_7$), 1.69-1.47 (m, 3H, H$_B$C$_7$, H$_2$C$_8$), 1.28 (s, 3H, H$_3$C$_{20}$), 1.05 (d, J=6.6 Hz, 3H, H$_3$C$_{21}$); $^{13}$C NMR (126 MHz, CDCl$_3$): δ 200.1 (C$_3$=O), 166.9 (C$_{15}$=O), 150.0 (C$_2$), 143.9 (C$_1$), 137.0 (C$_{Ar-ipso}$), 136.9 (C$_{Ar-ipso}$), 128.7 (C$_{Ar}$H), 128.6 (C$_{Ar}$H), 128.2 (C$_{Ar}$H), 128.1 (C$_{Ar}$H), 128.0 (C$_{Ar}$H), 127.7 (C$_{Ar}$H), 97.0 (BnOCH$_2$O), 91.4 (C$_6$), 90.6 (C$_{11}$), 89.8 (BnOCH$_2$O), 87.1 (C$_{12}$), 80.0 (Co$_1$H), 71.1 (PhCH$_2$O), 70.3 (PhCH$_2$O), 64.4 (C$_4$H), 45.1 (C$_5$), 39.1 (C$_{14}$H$_2$), 33.3 (C$_9$H), 27.9 (C$_8$H$_2$), 21.3 (C$_7$H$_2$), 19.9 (C$_{20}$H$_3$), 18.5 (C$_{21}$H$_3$), 11.2 (C$_{17}$H$_3$); FTIR (NaCl, thin film): 3350, 2926, 1744, 1707, 1405, 1240, 1157, 1034 cm$^{-1}$; HRMS: calc'd for [M+NH$_4$]$^+$: 596.2871, found: 596.2854; [α]$_D^{25}$: +79 (c=0.55, CHCl$_3$).

Treatment of 17 with excess SeO$_2$ in wet 1,4-dioxane at 110° C. not only effected C3-oxidation, but also the formal hydration of the enone, thereby installing the C12-alcohol and providing diosphenol 21. Enone 17 was subjected to SeO$_2$ under anhydrous conditions in the presence of 4 Å molecular sieves (4 Å MS). Prolonged heating at 110° C. in 1,4-dioxane provided a distinct product, which had incorporated an additional oxygen. See Scheme 4. Structural assignment of this compound revealed it to be the fully oxidized diosphenol 18, a compound with the C4, C12 syn-vicinal diol of 2

Scheme 5

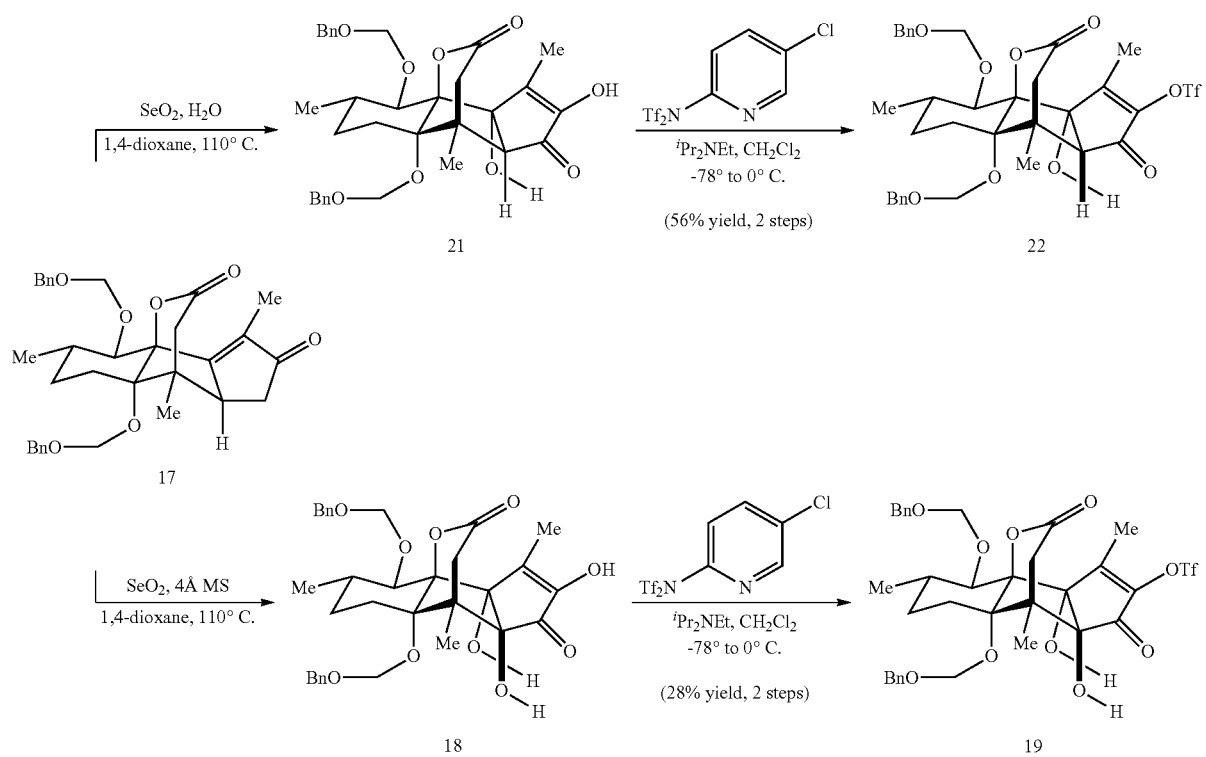

Example 12: Preparation of Triflate 22

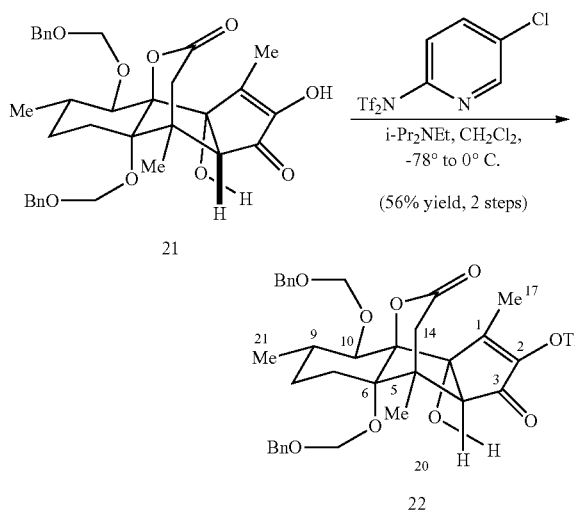

To a 25-mL, round-bottomed flask was added 21 (material directly isolated from the previous reaction) and anhydrous CH$_2$Cl$_2$ (4.0 mL). i-Pr$_2$NEt (0.18 ml) was added and then the solution was cooled to −78° C. in a dry ice/acetone bath. N-(5-chloro-2-pyridyl)bis(trifluoromethanesulfonimide) (Comins' reagent, 78.5 mg, 0.20 mmol, 1.0 equiv) was then added in a single portion and the solution stirred for 5 minutes, then the cold bath removed and replaced with an ice/water bath at 0° C. After 1 h, the solution was directly loaded onto a silica gel column (30 to 40% EtOAc in hexanes) to afford triflate 22 as a colorless foam (79.4 mg, 0.111 mmol, 56% yield).

TLC (40% EtOAc/Hexanes), R$_f$: 0.40 (UV, KMnO$_4$); $^1$H NMR (CDCl$_3$, 400 MHz): δ 7.41-7.29 (m, 10H, H—Ar), 5.33 (s, 1H, OH), 5.05 (d, J=4.7 Hz, 1H, BnOCH$_2$O), 4.99 (d, J=6.8 Hz, 1H BnOCH$_2$O), 4.95 (d, J=6.9 Hz, 1H, BnOCH$_2$O), 4.79 (d, J=4.8 Hz, 1H, BnOCH$_2$O), 4.77 (d, J=11.8 Hz, 1H, PhCH$_2$O), 4.71 (d, J=11.7 Hz, 1H, PhCH$_2$O), 4.64 (s, 2H, PhCH$_2$O), 4.01 (d, J=10.5 Hz, 1H, HC$_{10}$), 3.03 (d, J=1.5 Hz, 1H, HC$_4$), 2.49 (d, J=19.9 Hz, 1H, H$_A$C$_{14}$), 2.31 (dd, J=19.9, 1.5 Hz, 1H, H$_B$C$_{14}$), 2.26 (s, 3H, H$_3$C$_{17}$), 2.15-2.05 (m, 1H, HC$_9$), 1.96-1.88 (m, 1H, H$_A$C$_7$), 1.70-1.46 (m, 3H, H$_B$C$_7$, H$_2$C$_8$), 1.30 (s, 3H, H$_3$C$_{20}$), 1.01 (d, J=6.5 Hz, 3H, H$_3$C$_{21}$); $^{13}$C NMR (126 MHz, CDCl$_3$): δ 195.5 (C$_3$=O), 166.0 (C$_{15}$=O), 164.0 (C), 144.8 (C), 137.0 (C$_{Ar-ipso}$), 136.1 (C$_{Ar-ipso}$), 128.8 (C$_{Ar}$H), 128.7 (C$_{Ar}$H), 128.4 (C$_{Ar}$H), 128.2 (C$_{Ar}$H), 128.0 (C$_{Ar}$H), 127.8 (C$_{Ar}$H), 118.3 (q, J$_{C-F}$=321 Hz, SO$_2$CF$_3$), 96.6 (BnOCH$_2$O), 90.5 (C$_6$), 90.5 (C$_{11}$), 89.5 (BnOCH$_2$O), 86.0 (C$_{12}$), 79.5 (C$_{10}$H), 70.8 (PhCH$_2$O), 70.0 (PhCH$_2$O), 63.6 (C$_4$H), 45.7 (C$_5$), 38.8 (C$_{14}$H$_2$), 33.2 (C$_9$H), 27.8 (C$_8$H$_2$), 21.2 (C$_7$H$_2$), 19.8 (C$_{20}$H$_3$), 18.2 (C$_{21}$H$_3$), 12.6 (C$_{17}$H$_3$); FTIR (NaCl, thin film): 3368, 2930, 2875, 1756, 1732, 1426, 1216, 1038 cm$^{-1}$; HRMS: calc'd for [M+NH$_4$]$^+$: 728.2347, found 728.2359; [α]$_D^{25}$: +83 (c=1.0 CHCl$_3$).

Example 13: Preparation of Diosphenol 18

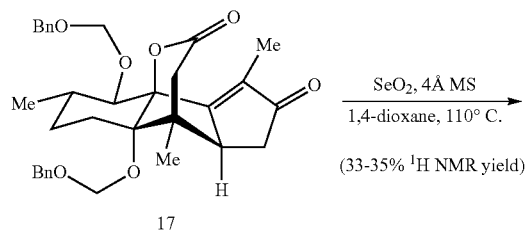

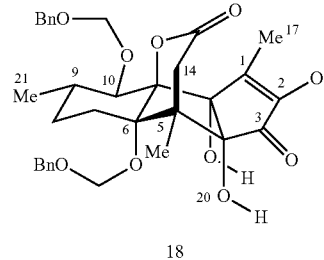

To an oven-dried, 48-mL, heavy-walled pressure vessel equipped with a magnetic stir bar was charged enone 17 (1.09 g, 2.00 mmol, 1.0 equiv), anhydrous $SeO_2$ (2.22 g, 20.0 mmol, 10.0 equiv), and freshly activated 4 Å molecular sieves (prepared via vigorous flame-drying at <200 mTorr for 10 minutes, 2.18 g, 200 wt % relative to substrate) in a nitrogen-filled glovebox. Anhydrous 1,4-dioxane (20 mL) was then added and the vessel was tightly sealed, removed from the glovebox, and submerged in a preheated oil bath at 110° C. After 9.0 h, the vessel was allowed to cool to ambient temperature, diluted with EtOAc (100 mL), and filtered through a short pad of Celite, rinsing with additional EtOAc (50 mL). The resulting filtrate was then washed with sat. aq. $NaHCO_3$ (2×50 mL), $H_2O$ (50 mL), and the combined aqueous layers back extracted with EtOAc (2×25 mL). The combined organics were then dried over anhydrous $Na_2SO_4$, filtered, and concentrated in vacuo to afford an orange foam. $^1H$ NMR analysis of this crude reaction mixture, integrating an external standard of phenyltrimethylsilane, indicated that 18 had been produced in 34% $^1H$ NMR yield. The crude residue was purified via silica gel chromatography (slurry packed column, 2% MeOH in $CH_2Cl_2$) to afford a pale orange-tan foam. The isolated material (typically ~575 mg) was carried to the next reaction without further purification.

A sample of this material was further purified by repeated silica gel chromatography for characterization purposes.

TLC (70% EtOAc/Hexanes), $R_f$: 0.36 (UV, $KMnO_4$); $^1H$ NMR (500 MHz, $CDCl_3$): δ 7.40-7.27 (m, 10H, H—Ar), 5.66 (br s, 1H, $HOC_2$), 5.15 (d, J=5.7 Hz, 1H, $BnOCH_2O$), 4.96 (d, J=6.1 Hz, 1H, $BnOCH_2O$), 4.93 (d, J=6.2 Hz, 1H, $BnOCH_2O$), 4.89 (d, J=5.7 Hz, 1H, $BnOCH_2O$), 4.76 (d, J=12.1 Hz, 1H, $PhCH_2O$), 4.72 (d, J=11.7 Hz, 1H, $PhCH_2O$), 4.68 (d, J=11.7 Hz, 1H, $PhCH_2O$), 4.65 (d, J=12.1 Hz, 1H, $PhCH_2O$), 4.60 (s, 1H, OH), 4.08 (s, 1H, OH), 4.00 (d, J=10.5 Hz, 1H, $HC_{10}$), 2.41 (d, J=19.8 Hz, 1H, $H_AC_{14}$), 2.25 (d, J=19.9 Hz, 1H, $H_BC_{14}$), 2.14 (s, 3H, $H_3C_{17}$), 2.13-2.00 (m, 1H, $HC_9$), 1.92-1.81 (m, 1H, $H_AC_7$), 1.64 (dtd, J=6.7, 4.6, 2.1 Hz, 1H, $H_AC_8$), 1.56-1.42 (m, 2H, $H_BC_7$, $H_BC_8$), 1.27 (s, 3H, $H_3C_{20}$), 1.08 (d, J=6.6 Hz, 3H, $H_3C_{21}$); $^{13}C$ NMR (126 MHz, $CDCl_3$): δ 197.2 ($C_3$=O), 166.7 ($C_{15}$=O), 149.3 ($C_2$), 146.0 ($C_1$), 137.0 ($C_{Ar-ipso}$), 136.4 ($C_{Ar-ipso}$), 128.7 ($C_{Ar}H$), 128.6 ($C_{Ar}H$), 128.4 ($C_{Ar}H$), 128.1 ($C_{Ar}H$), 128.0 ($C_{Ar}H$), 127.8 ($C_{Ar}H$), 97.1 ($BnOCH_2O$), 91.2 ($C_6$), 90.6 ($C_{11}$), 90.2 ($BnOCH_2O$), 86.6 ($C_{12}$), 84.6 ($C_4$), 79.9 ($C_{10}H$), 71.7 ($PhCH_2O$), 70.4 ($PhCH_2O$), 47.3 ($C_5$), 40.8 ($C_{14}H_2$), 33.1 ($C_9H$), 27.9 ($C_8H_2$), 21.5 ($C_7H_2$), 18.6 ($C_{21}H_3$), 15.1 ($C_{20}H_3$), 11.3 ($C_{17}H_3$); FTIR (NaCl, thin film): 3368, 2928, 1747, 1717, 1659, 1454, 1405, 1360, 1155, 1035 $cm^{-1}$; HRMS: calc'd for $[M+Na]^+$: 617.2357, found: 617.2367; $[α]_D^{25}$: +120 (c=0.86, $CHCl_3$).

Example 14: Preparation of Vinyl Triflate 19

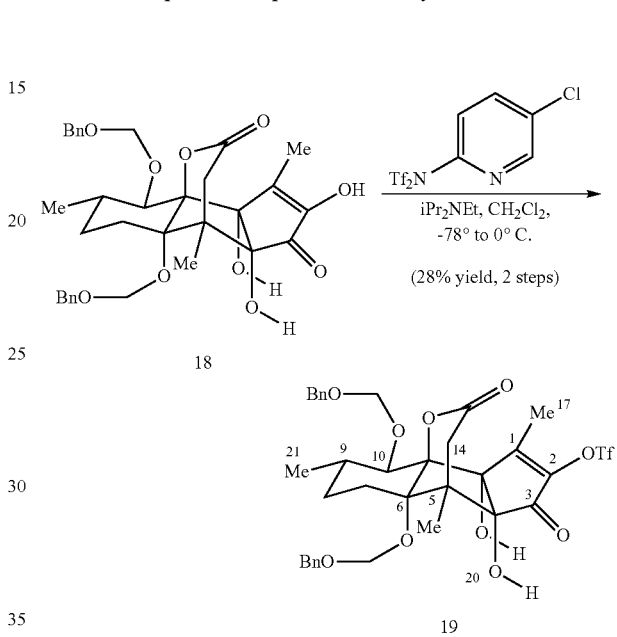

To a 50-mL, round-bottomed flask was added 18 (directly from the previous reaction, approximately 575 mg) and anhydrous $CH_2Cl_2$ (20 mL). $iPr_2NEt$ (0.89 mL) was added, and then the solution was cooled to −78° C. in a dry ice/acetone bath. N-(5-chloro-2-pyridyl) bis(trifluoromethanesulfonimide) (Comins' reagent, 589 mg, 1.50 mmol) was then added in a single portion and the solution stirred for five minutes, then the cold bath removed and replaced with an ice/water bath at 0° C. After 1 h, the solution was directly purified by silica gel chromatography (30 to 40% EtOAc in Hexanes) to afford triflate 19 as a slightly off white foam (413 mg, 0.568 mmol, 28% yield, 2 steps).

TLC(40% EtOAc/Hexanes), $R_f$: 0.36 (UV, $KMnO_4$); $^1H$ NMR ($CDCl_3$, 400 MHz): δ 7.41-7.28 (m, 10H, H—Ar), 5.09 (d, J=5.4 Hz, 1H, $BnOCH_2O$), 4.98 (s, 1H, OH), 4.95 (d, J=6.2 Hz, 1H, $BnOCH_2O$), 4.93 (d, J=6.2 Hz, 1H, $BnOCH_2O$), 4.88 (d, J=5.4 Hz, 1H, $BnOCH_2O$), 4.73 (d, J=12.2 Hz, 1H, $PhCH_2O$), 4.69 (m, 2H, $PhCH_2O$), 4.65 (d, J=12.0 Hz, 1H, $PhCH_2O$), 4.21 (s, 1H, OH), 3.98 (d, J=10.5 Hz, 1H, $HC_{10}$), 2.53 (d, J=20.3 Hz, 1H, $H_AC_{14}$), 2.44 (d, J=20.2 Hz, 1H, $H_BC_{14}$), 2.30 (s, 3H, $H_3C_{17}$), 2.08 (tdd, J=13.8, 7.0, 3.9 Hz, 1H, $HC_9$), 1.93-1.83 (m, 1H, $H_AC_7$), 1.70-1.60 (m, 1H, $H_AC_8$), 1.54-1.44 (m, 2H, $H_BC_7$, $H_BC$), 1.28 (s, 3H, $H_3C_{20}$), 1.07 (d, J=6.6 Hz, 3H, $H_3C_{21}$); $^{13}C$ NMR (126 MHz, $CDCl_3$): δ 192.9 ($C_3$=O), 165.6 ($C_{15}$=O), 164.6 (C), 144.4 (C), 136.6 ($C_{Ar-ipso}$), 136.2 ($C_{Ar-ipso}$), 128.8 ($C_{Ar}H$), 128.7 ($C_{Ar}H$), 128.5 ($C_{Ar}H$), 128.2 ($C_{Ar}H$), 128.1 ($C_{Ar}H$), 127.8 ($C_{Ar}H$), 118.3 (q, $J_{C-F}$=321 Hz, $SO_2CF_3$), 96.8 ($BnOCH_2O$), 90.6 ($C_6$), 90.4 ($C_{11}$), 90.2 ($BnOCH_2O$), 85.7 ($C_{12}$), 84.4 ($C_4$), 79.5 ($C_{10}H$), 71.8

(PhCH₂O), 70.4 (PhCH₂O), 47.6 (C₅), 40.1 (C₁₄H₂), 33.0 (C₉H), 27.8 (C₈H₂), 21.4 (C₇H₂), 18.4 (C₂₁H₃), 15.1 (C₂₀H₃), 12.7 (C₁₇H₃); FTIR (NaCl, thin film): 3368, 2931, 1743, 1650, 1429, 1243, 1216, 1040 cm⁻¹; HRMS: calc'd for [M+NH₄]⁺: 744.2313, found: 744.2296; [α]$_D^{25}$: +58 (c=0.74, CHCl₃).

Example 15: Preparation of Enone 20

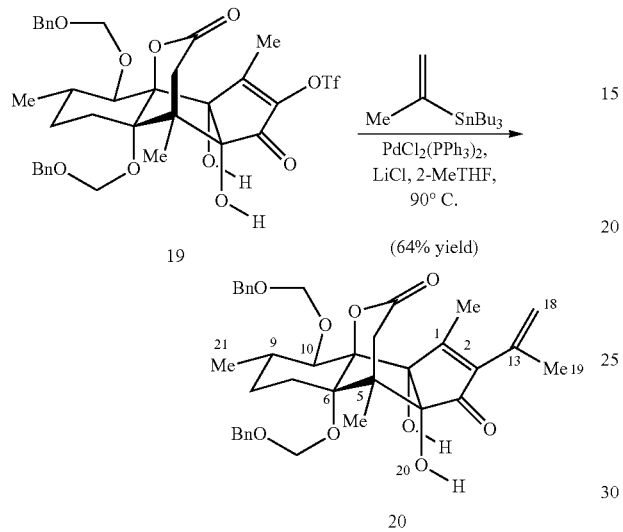

In a nitrogen-filled glovebox, an oven-dried, 48-mL capacity heavy-walled pressure vessel was charged with vinyl triflate 19 (413 mg, 0.568 mmol, 1.0 equiv), PdCl₂(PPh₃)₂ (159 mg, 0.227 mmol, 40 mol %), anhydrous LiCl (192 mg, 4.54 mmol, 8.0 equiv), tributyl(2-propenyl)stannane (752 mg, 2.27 mmol, 4.0 equiv), and anhydrous 2-methyltetrahydrofuran (11 mL). The vial was sealed with a PTFE-lined cap, and submerged in a preheated oil bath at 90° C. After 14 h, the vial was removed from the bath and allowed to cool to ambient temperature, then sat. aq. KF (15 mL) was added. The solution was stirred for 45 minutes, diluted with EtOAc (50 mL) and washed with sat. aq. KF (20 mL). The combined aqueous layers were extracted with additional EtOAc (25 mL), and the combined organics washed with brine (50 mL), dried over anhydrous Na₂SO₄, filtered over Celite, and concentrated in vacuo to afford a red-brown oil. Purification by silica gel chromatography (30 to 40% EtOAc in hexanes) afforded enone 20 as an off-white foam (224 mg, 0.363 mmol, 64% yield).

TLC (40% EtOAc/Hexanes), R$_f$: 0.32 (UV, KMnO₄); ¹H NMR (CDCl₃, 400 MHz): 7.40-7.27 (m, 10H, H—Ar), 5.24 (p, J=1.6 Hz, 1H, H$_A$C₁₈), 5.15 (d, J=5.9 Hz, 1H, BnOCH₂O), 4.96 (d, J=6.3 Hz, 1H, BnOCH₂O), 4.94 (d, J=6.3 Hz, 1H, BnOCH₂O), 4.92 (d, J=5.9 Hz, 1H, BnOCH₂O), 4.82 (dq, J=2.0, 1.0 Hz, 1H, H$_A$C₁S), 4.78 (d, J=12.1 Hz, 1H, PhCH₂O), 4.70 (s, 2H, PhCH₂O), 4.64 (d, J=12.1 Hz, 1H, PhCH₂O), 4.27 (s, 1H, OH), 4.01 (d, J=10.5 Hz, 1H), 3.94 (s, 1H, OH), 2.42 (d, J=19.8 Hz, 1H, H$_A$C₁₄), 2.32 (d, J=19.8 Hz, 1H, H$_B$C₁₄), 2.25 (s, 3H, H₃C₁₇), 2.14-2.01 (m, 1H, HC₉), 1.89-1.82 (m, 1H, H$_A$C₇), 1.87 (q, J=1.5 Hz, 3H, H₃C₁₉), 1.65 (dtt, J=7.9, 4.9, 2.2 Hz, 1H, H$_A$C₈), 1.54-1.46 (m, 2H, H$_B$C, H$_B$C), 1.26 (s, 3H, H₃C₂₀), 1.10 (d, J=6.5 Hz, 3H, H₃C₂₁); ¹³C NMR (126 MHz, CDCl₃): δ 202.1 (C₃═O), 171.0 (C₁₅═O), 166.8 (C₁), 143.7 (C₂), 137.3 (C), 136.5 (C), 135.6 (C), 128.7 (C$_{Ar}$H), 128.5 (C$_{Ar}$H), 128.4 (C$_{Ar}$H), 128.1 (C$_{Ar}$H), 127.9 (C$_{Ar}$H), 127.7 (C$_{Ar}$H), 118.2 (C₁₈H₂), 97.1 (BnOCH₂O), 91.3 (C₆), 91.2 (C₁₁), 90.3 (BnOCH₂O), 88.1 (C), 85.5 (C), 79.9 (HC₁₀), 71.8 (PhCH₂O), 70.5 (PhCH₂O), 47.6 (C₅), 40.9 (C₁₄H₂), 33.1 (C₉H), 27.9 (C₈H₂), 21.6 (C₁₉H₃), 21.4 (C₇H₂), 18.7 (C₂₁H₃), 15.0 (C₂₀H₃), 15.0 (C₁₇H₃); FTIR (NaCl, thin film): 3412, 2953, 2925, 1749, 1709, 1037, 1026 cm⁻¹; HRMS: calc'd for [M+Na]⁺: 641.2721, found: 641.2729; [α]$_D^{25}$: +100 (c=0.67, CHCl₃).

Example 16: Preparation of Enone SI-3

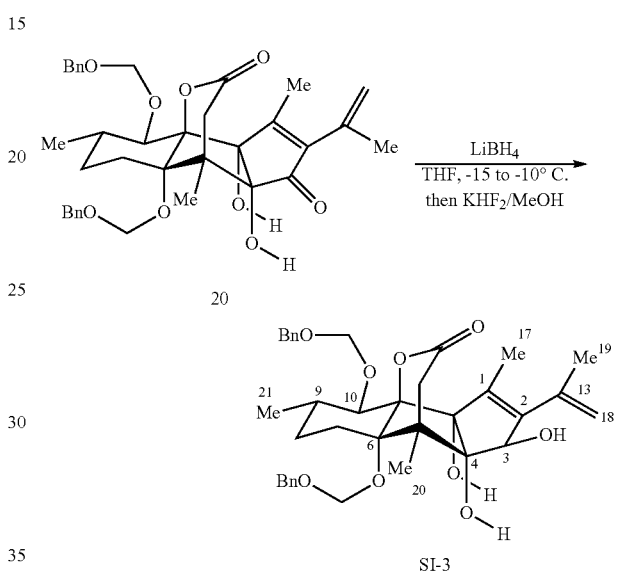

To an oven-dried, 2-dram vial was added enone 20 (250 mg, 0.404 mmol, 1.00 equiv), and anhydrous THF (16 mL). The solution was cooled to −15° C. in an ice/MeOH bath and solid LiBH₄ (132 mg, 6.06 mmol, 15 equiv) was added in a single portion. The temperature was carefully maintained between −10 and −15° C. After 2 h, TLC analysis indicated full consumption of the starting material. Sat. aq. NH₄Cl was then slowly added to the reaction. The mixture was diluted with EtOAc (30 mL), and washed thoroughly with sat. aq. NH₄Cl (2×20 mL), and the combined organic layers extracted with additional EtOAc (20 mL). The solution was then concentrated in vacuo, redissolved in MeOH (45 mL) and KHF₂ (3 M in H₂O, 3 mL) was then added and the solution vigorously swirled for two minutes and the entire mixture concentrated in vacuo [rotary evaporator bath temperature at 35° C.]. The resultant residue was suspended in EtOAc (50 mL), anhydrous Na₂SO₄ added, then filtered through a short pad of silica gel to remove salts, and rinsed with additional EtOAc (25 mL), concentrated in vacuo. The resulting off-white foam was carried onto the next step without further purification.

A sample of allylic alcohol SI-3 could be additionally purified by preparative thin-layer chromatography (30% EtOAc in CH₂Cl₂) for characterization purposes.

TLC (40% EtOAc/Hexanes), R$_f$: 0.12 (UV, KMnO₄); ¹H NMR (CDCl₃, 400 MHz): δ 7.42-7.26 (m, 10H, H—Ar), 5.17 (d, J=6.5 Hz, 1H, BnOCH₂O), 5.16-5.14 (m, 1H, H$_A$C₁₈), 4.99 (d, J=5.9 Hz, 1H, BnOCH₂O), 4.95 (d, J=5.8 Hz, 1H, BnOCH₂O), 4.87 (d, J=6.3 Hz, 1H, BnOCH₂O), 4.89-4.87 (m, 1H, H$_B$C₁₈), 4.86-4.83 (m, 1H, HC₃), 4.79 (d, J=12.3 Hz, 1H, PhCH$_2$O), 4.73 (d, J=11.8 Hz, 1H, PhCH$_2$O), 4.69 (d, J=11.8 Hz, 1H, PhCH$_2$O), 4.61 (d, J=12.2 Hz, 1H, PhCH$_2$O), 4.41 (s, 1H, OH), 3.91 (d, J=10.3 Hz, 1H, HC$_{10}$), 3.89 (s, 1H, OH), 3.53 (d, J=19.8 Hz, 1H, H$_A$C$_{14}$), 2.26 (d, J=19.8 Hz, 1H, H$_B$C$_{14}$), 2.13-2.03 (m, 1H, HC$_9$), 2.08 (d, J=4.6 Hz, 1H, C$_3$OH), 1.85 (d, J=2.3 Hz, 3H, H$_3$C$_{17}$), 1.85-1.83 (m, 3H, H$_3$C$_{19}$), 1.79 (ddd, J=14.9, 4.4, 2.1 Hz, 1H, H$_A$C$_7$), 1.71-1.63 (m, 1H, H$_A$C$_8$), 1.56 (ddd, J=14.9, 12.9, 4.6 Hz, 1H, H$_B$C$_7$), 1.38-1.27 (m, 1H, H$_B$C$_8$), 1.30 (s, 3H, H$_3$C$_{20}$), 1.09 (d, J=6.5 Hz, 3H, H$_3$C$_{21}$); $^{13}$C NMR (126 MHz, CDCl$_3$): δ 168.5 (C$_{15}$=O), 143.4 (C), 138.4 (C), 137.7 (C), 136.6 (C), 136.4 (C), 128.7 (C$_{Ar}$H), 128.4 (C$_{Ar}$H), 128.2 (C$_{Ar}$H), 127.7 (C$_{Ar}$H), 127.7 (C$_{Ar}$H), 117.0 (C$_{18}$H$_2$), 97.3 (BnOCH$_2$O), 91.5 (C), 91.2 (C), 91.1 (C), 90.4 (BnOCH$_2$O), 88.7 (C), 83.0 (C$_3$H), 80.6 (C$_{10}$H), 72.1 (PhCH$_2$O), 70.5 (PhCH$_2$O), 49.2 (C$_5$), 39.6 (C$_{14}$H$_2$), 33.2 (C$_9$H), 28.3 (C$_8$H$_2$), 21.3 (C$_{19}$H$_3$), 21.2 (C$_7$H$_2$), 18.9 (C$_{21}$H$_3$), 16.0 (C$_{20}$H$_3$), 13.0 (C$_{17}$H$_3$); FTIR (NaCl, thin film): 3453, 2923, 2872, 1742, 1026 cm$^{-1}$; HRMS: calc'd for [M+Na]$^+$: 643.2878, found: 643.2886; [α]$_D^{25}$: −29 (c=0.33, CHCl$_3$).

Example 17: Preparation of Anhydroryanodol (3)

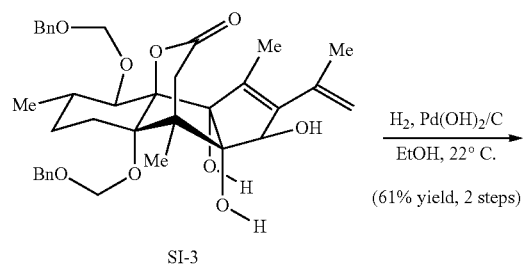

SI-3

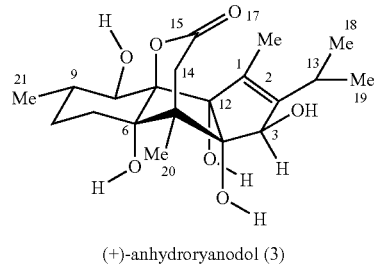

(+)-anhydroryanodol (3)

To a 25-mL, round-bottomed flask was charged crude triol SI-3. Pd(OH)$_2$/C (20 wt %, 375 mg) was added, followed by absolute EtOH (16 mL). The suspension was sparged with N$_2$ for five minutes, then H$_2$ for 5 minutes via a double-walled balloon. The suspension was subsequently stirred for 2 h at 20° C. under H$_2$, sparged with N$_2$ to remove excess hydrogen gas, then diluted with EtOAc (50 mL), filtered through a short pad of Celite and concentrated in vacuo. Purification of the crude residue by silica gel chromatography (slurry packed column, 4% MeOH in CHCl$_3$) affords (+)-anhydroryanodol (3) (94.1 mg, 0.246 mmol, 61% yield) as a colorless foam.

TLC (10% MeOH/CH$_2$Cl$_2$), R$_f$: 0.32 (KMnO$_4$); $^1$H NMR (500 MHz, CD$_3$OD): δ 4.71 (q, J=2.3 Hz, 1H, HC$_3$), 3.98 (d, J=10.4 Hz, 1H, HC$_{10}$), 3.62 (d, J=19.9 Hz, 1H, H$_A$C$_{14}$), 2.75 (hept, J=7.0 Hz, 1H, HC$_{13}$), 2.30 (d, J=19.8 Hz, 1H, H$_B$C$_{14}$), 1.84-1.74 (m, 1H, HC$_9$), 1.77 (d, J=2.4 Hz, 3H, H$_3$C$_{17}$), 1.62-1.43 (m, 4H, H$_2$C$_7$, H$_2$C$_8$), 1.18 (s, 3H, H$_3$C$_{20}$), 1.15 (d, J=7.0 Hz, 3H, H$_3$C$_{18}$), 1.11 (d, J=7.0 Hz, 3H, H$_3$C$_{19}$), 1.08 (d, J=6.5 Hz, 3H, H$_3$C$_{21}$); $^{13}$C NMR (126 MHz, CD$_3$OD): δ 173.2 (C$_{15}$=O), 148.3 (C$_2$), 134.2 (C$_1$), 93.4 (C$_{12}$), 92.8 (C$_{11}$), 90.3 (C$_4$), 84.7 (C$_6$), 84.0 (C$_3$H), 72.8 (C$_{10}$H), 48.9 (C$_5$), 40.3 (C$_{14}$H$_2$), 35.2 (C$_9$H), 28.8 (C$_8$H$_2$), 28.5 (C$_{13}$H), 26.1 (C$_7$H$_2$), 21.6 (C$_{19}$H$_3$), 19.3 (C$_{18}$H$_3$), 18.8 (C$_{21}$H$_3$), 14.7 (C$_{20}$H$_3$), 12.2 (C$_{17}$H$_3$); FTIR (NaCl, thin film): 3450, 1735 cm$^{-1}$; HRMS: calc'd for [M−H]: 381.1919, found: 381.2045; [α]$_D^{25}$: +54 (c=0.45, MeOH).

Example 18: Preparation of Epianhydroryanodol Epoxide (SI-4

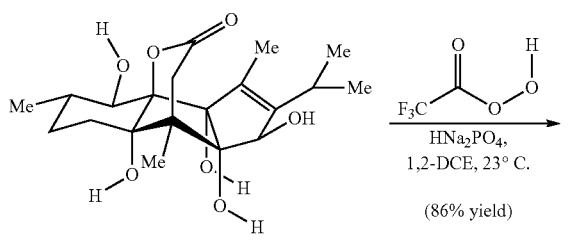

(+)-anhydroryanodol (3)

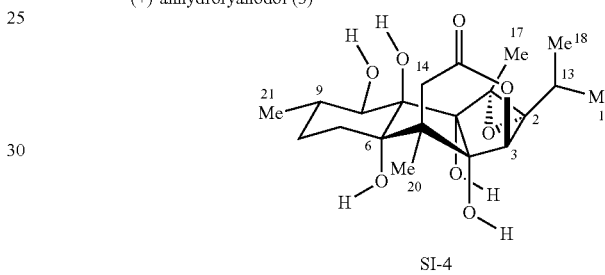

SI-4

An approximately 1M solution of trifluoroperacetic acid was prepared according to the following procedure: to a 25-mL, round-bottomed flask was added urea hydrogen peroxide (940 mg, 10.0 mmol, 1.00 equiv) and anhydrous 1,2-dichloroethane (10.0 mL). The suspension was cooled to 0° C. in an ice/water bath and trifluoroacetic anhydride (1.56 mL, 11 mmol, 1.1 equiv) added dropwise by syringe. The solution was stirred at 0° C. for 1 h, then the ice bath removed and stirred at 20° C. for 1 h, by which time the white suspension had changed into a biphasic mixture. Stirring was stopped to allow the layers to separate before addition.

To a 100-mL, round-bottomed flask was added anhydroryanodol (76.4 mg, 0.200 mmol, 1.00 equiv), HNa$_2$PO$_4$ (170 mg, 1.20 mmol, 6.0 equiv) and 1,2-dichloroethane (30 mL). The suspension was stirred vigorously at 20° C., then trifluoroperacetic acid (1M solution in 1,2-DCE, as prepared above, 0.40 mL, ~0.40 mmol, ~2 equiv) was added dropwise by syringe. The solution was stirred for 3 h at 20° C., by which time TLC analysis had indicated consumption of the starting material, then filtered over a short pad of Celite to remove solids, rinsing with 1,2-dichloroethane (20 mL) and concentrated in vacuo to afford a white foam. Purification of the crude foam by silica gel chromatography (5% MeOH in CHCl$_3$) afforded epianhydroryanodol epoxide SI-4 as a colorless semicrystalline solid (68.5 mg, 0.172 mmol, 86% yield).

TLC (5% MeOH/CH$_2$Cl$_2$), R$_f$ 0.20 (KMnO$_4$); $^1$H NMR (CD$_3$OD, 400 MHz): δ 4.58 (s, 1H, HC$_3$), 4.07 (d, J=10.1 Hz, 1H, HC$_{10}$), 3.66 (d, J=16.0 Hz, 1H, H$_A$C$_{14}$), 2.18 (d, J=16.1 Hz, 1H, H$_B$C$_{14}$), 1.87-1.76 (m, 2H, H$_A$C$_7$, HC$_{13}$), 1.73-1.64 (m, 1H, HC$_9$), 1.63 (s, 3H, H$_3$C$_{17}$), 1.59-1.41 (m, 2H, H$_2$C$_8$), 1.29 (ddd, J=13.0, 4.5, 2.1 Hz, 1H, H$_B$C$_7$), 1.22 (d, J=7.0 Hz, H$_3$C$_{19}$), 1.06 (d, J=7.3 Hz, 3H, H$_3$C$_{18}$), 1.06 (d, J=6.3 Hz, 3H, H$_3$C$_{21}$), 1.01 (s, 3H, H$_3$C$_{20}$); $^{13}$C NMR (CD$_3$OD, 400 MHz): 174.2 (C$_{15}$=O), 94.7 (C), 89.8 (C$_3$H), 89.1 (C), 88.1 (C), 85.1 (C), 77.4 (C), 74.8 (C), 74.3 (C$_{10}$H), 51.0 (C$_5$), 38.4 (C$_{14}$H$_2$), 34.6 (C$_9$H), 30.6 (C$_{13}$H), 28.5 (C$_8$H$_2$), 24.7 (C$_7$H$_2$), 19.1 (C$_{19}$H$_3$), 18.3 (C$_{20}$H$_3$), 17.4 (C$_{18}$H$_3$), 17.1 (C$_{21}$H$_3$), 15.2 (C$_{17}$H$_3$); FTIR (NaCl, thin film): 3462, 1736 cm$^{-1}$; HRMS: calc'd for [M+H]$^+$: 399.2013, found: 399.2034. [α]$_D^{25}$: −39 (c=0.40, MeOH).

Example 19: Preparation of (+)-Ryanodol (2)

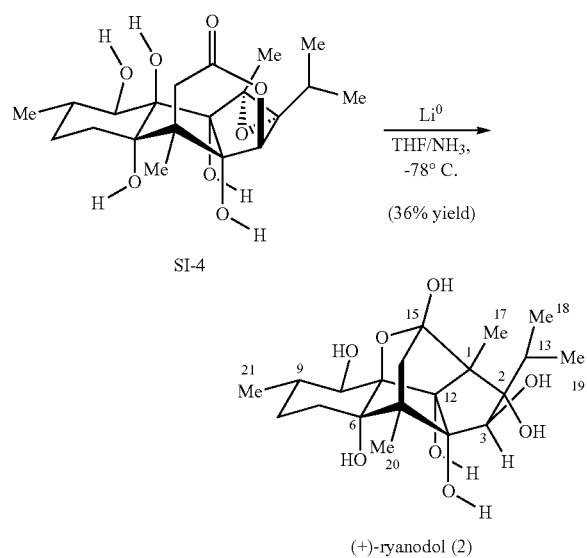

An oven-dried, 100-mL, three-necked, round-bottomed flask containing a borosilicate glass-coated magnetic stir bar was equipped with an oven-dried cold-finger condenser and allowed to cool under dry Argon. While cooling, the flask was directly connected to a gas cylinder of ammonia (Matheson anhydrous ammonia) by means of a gas inlet adapter connected to a piece of dry Tygon tubing. Once the glassware had completely cooled, the flask was submerged into a dry-ice/acetone bath (−78° C.) and the cold finger filled with dry-ice/acetone. Ammonia was carefully condensed into the flask by opening the tank, until ~50 mL had accumulated, and both the ammonia inlet and cold finger condenser were removed and replaced with rubber septa. Freshly cut sodium metal (200 mg cut into six pieces, hexanes washed) was then added piecewise to the ammonia, which resulted immediately in a deep blue solution. This solution was maintained at −78° C. for 30 min for drying.

A separate oven-dried, 100-mL, three-necked, round-bottomed flask containing a borosilicate glass coated magnetic stir bar was equipped with an oven-dried cold-finger condenser, and was allowed to cool under an Ar atmosphere. The distilling flask prepared above was then connected by means of a dry piece of Tygon tubing under a positive pressure of Argon. The receiving flask was submerged into a dry-ice/acetone bath, and the cold finger condenser filled with dry ice/acetone. The distilling flask was then removed from the cold bath, allowing for the slow distillation of anhydrous ammonia from sodium metal, until ~20 mL of ammonia had condensed into the receiving flask (approximately 30 minutes). A solution of epianhydroryanodol epoxide (SI-4, 15.3 mg, 38.7 µmol, 1.0 equiv) in THF (4.0 mL) was then added dropwise by syringe to the freshly distilled ammonia, which was allowed to stir for an additional 15 minutes −78° C.

A fresh piece of lithium-wire (30.5 mg, stored in mineral oil), was rinsed with hexanes, then cut into a pre-tared 25-mL beaker containing hexanes (15 mL). Immediately prior to addition, this piece of wire was further cut into four pieces (~7-8 mg each) and added to the flask above within two minutes, and the deep blue mixture stirred for 60 min at −78° C. Ammonium chloride (solid, 750 mg) was then added slowly as a solid. The deep blue color faded within 90 seconds, producing a colorless suspension. The cold bath was then removed and the flask was opened to atmosphere, allowing for the evaporation of ammonia as the flask warmed to ambient temperature (45 min). The resulting slurry, consisting primarily of some residual THF, LiCl, and NH$_4$Cl salts, was then carefully diluted with H$_2$O (20 mL), and additional THF (5 mL). The mixture was extracted with CH$_2$Cl$_2$ (3×15 mL), and the combined organics concentrated in vacuo. $^1$H NMR analysis of this organic layer indicated the presence of a carbonyl reduction product and a small amount of starting material.

Carbon dioxide (g) was then bubbled through the aqueous layer (20 mL) for 10 minutes to neutralize the pH below 8 and the aqueous layer saturated with NaCl. This aqueous solution was then transferred into a continuous extraction apparatus equipped with an efficient reflux condenser and 100 mL round bottomed flask that had been pre-filled with CHCl$_3$ (50 mL in the flask, 100 mL in the extraction body). The round-bottomed flask was then heated in an oil bath at 100° C., allowing for vigorous reflux of the chloroform, and the apparatus maintained for 40 h under a nitrogen atmosphere. The flask was then removed from the apparatus and the solvent removed in vacuo affording a solid residue. $^1$H NMR analysis of this organic residue indicated that it was ~90% pure by NMR. The residue was again dissolved in H$_2$O (20 mL) and THF (5 mL) and washed with CH$_2$Cl$_2$ (3×15 mL). Concentration of the aqueous layer (rotovap temperature at 50° C.) and drying under high vacuum affords (+)-ryanodol (2) as a white solid (95% purity by $^1$H NMR, 7.4 mg, 47% yield) that contains minor salt impurities and is further purified by silica gel chromatography (3 g of slurry packed silica, 10% MeOH in CHCl$_3$) to afford ryanodol (2) as a white film (5.9 mg, 14.8 µmol, 38% yield).

A continuous extractor consisting of a 14/20 ground glass attachment was used for the extraction process. This particular extractor had a volume of approximately 120 mL, allowing for an aqueous phase of approximately 20 mL and a heavy-organic phase of 100 mL. Material obtained after continuous extraction was typically of ~90% purity by $^1$H NMR. Most organic impurities were readily removed by washing with THF/DCM, as described above. However, dissolution of this material in MeOH typically left trace inorganic residues (potentially trace salts from the aqueous phase) that affect an accurate mass. The material obtained after column chromatography does not produce the same residue, lending further evidence to trace inorganic salt impurities.

$^1$H NMR (CD$_3$OD, 400 MHz): δ 4.12 (s, 1H, HC$_3$), 3.78 (d, J=10.2 Hz, 1H, HC$_{10}$), 2.51 (d, J=13.4 Hz, 1H, H$_A$C$_{14}$), 2.15 (hept, J=6.7 Hz, 1H, HC$_3$), 2.08 (td, J=12.9, 5.3 Hz, 1H, H$_B$C$_7$), 1.90-1.76 (m, 1H, HC$_9$), 1.74 (d, J=13.4 Hz, 1H, H$_B$C$_{14}$), 1.53 (dtd, J=12.7, 5.2, 1.6 Hz, 1H, H$_B$C$_8$), 1.46 (qd, J=12.9, 4.7 Hz, 1H, H$_A$C$_8$), 1.33 (s, 3H, HC$_{17}$), 1.26 (ddd, J=12.7, 4.6, 2.0 Hz, 1H, H$_A$C$_7$), 1.12 (s, 3H, H$_3$C$_{20}$), 1.08 (d, J=6.8 Hz, 3H, $H_3C_{19}$), 1.01 (d, J=6.5 Hz, 3H, $H_3C_{21}$), 1.00 (d, J=6.5 Hz, 3H, $H_3C_{18}$). $^{13}$C NMR (CD$_3$OD, 400 MHz): δ 103.1 ($C_{15}$), 96.3 ($C_{12}$), 92.6 ($C_4$), 91.6 ($C_3$H), 87.3 ($C_{11}$), 86.6 ($C_6$), 84.9 ($C_2$), 72.9 ($C_{10}$H), 65.4 ($C_1$), 49.7 ($C_5$), 41.5 ($C_{14}H_2$), 35.4 ($C_9$H), 30.7 ($C_{13}$H), 29.4 ($C_8H_2$), 26.6 ($C_7H_2$), 19.5 ($C_{19}H_3$), 19.4 ($C_{18}H_3$), 19.0 ($C_{21}H_3$), 13.2 ($C_{20}H_3$), 10.2 ($C_{17}H_3$); HRMS: calc'd for [M−H]$^-$: 399.2024, found: 399.2028; $[\alpha]_D^{25}$: +37 (c=0.30, MeOH).

TABLE 2

Comparison of $^1$H NMR data for Authentic vs. Synthetic (+)-Ryanodol

| Carbon No. | Authentic Ryanodol (from hydrolysis of ryanodine) Inoue, 2014 (400 MHz, CD$_3$OD) $[\alpha]_D^{22} = +36$ (c 0.41, MeOH) $^1$H [δ, multi., J (Hz)] | Synthetic (+)-Ryanodol This disclosure (500 MHz, CD$_3$OD) $[\alpha]_D^{25}$: +37 (c = 0.30, MeOH) $^1$H [δ, multi., J (Hz)] |
|---|---|---|
| 1 | — | — |
| 2 | — | — |
| 3 | 4.12 (s, 1H) | 4.12 (s, 1H) |
| 4 | — | — |
| 5 | — | — |
| 6 | — | — |
| 7a | 1.26 (1H, ddd, J = 12.8, 4.6, 1.7 Hz) | 1.26 (ddd, J = 12.7, 4.6, 2.0 Hz, 1H) |
| 7b | 2.08 (ddd, J = 12.8, 12.8, 5.5 Hz, 1H) | 2.08 (td, J = 12.9, 5.3 Hz, 1H) |
| 8a | 1.45 (dddd, J = 13.2, 3.2, 12.8, 4.6 Hz, 1H) | 1.46 (qd, J = 12.9, 4.7 Hz, 1H) |
| 8b | 1.51 (dddd, J = 13.2, 5.8, 5.5, 1.7 Hz, 1H) | 1.53 (dtd, J = 12.7, 5.2, 1.6 Hz, 1H) |
| 9 | 1.83 (ddqd, J = 13.2, 10.4, 6.3, 5.8 Hz, 1H) | 1.90-1.76 (m, 1H) |
| 10 | 3.77 (d, J = 10.4 Hz, 1H) | 3.78 (d, J = 10.2 Hz, 1H) |
| 11 | — | — |
| 12 | — | — |
| 13 | 2.15 (qq, J = 6.8, 6.3 Hz) | 2.15 (hept, J = 6.7 Hz, 1H) |
| 14a | 1.73 (d, J = 13.1 Hz, 1H) | 1.74 (d, J = 13.4 Hz, 1H) |
| 14b | 2.51 (d, J = 13.1 Hz, 1H) | 2.51 (d, J = 13.4 Hz, 1H) |
| 15 | — | — |
| 17 | 1.33 (s, 3H) | 1.33 (s, 3H) |
| 18 | 1.00 (d, J = 6.3 Hz, 3H) | 1.00 (d, J = 6.5 Hz, 3H) |
| 19 | 1.08 (d, J = 6.8 Hz, 3H) | 1.08 (d, J = 6.8 Hz, 3H) |
| 20 | 1.12 (s, 3H) | 1.12 (s, 3H) |
| 21 | 1.01 (d, J = 6.3 Hz, 3H) | 1.01 (d, J = 6.5 Hz, 3H) |

TABLE 3

Comparison of $^{13}$C NMR data for Authentic vs. Synthetic (+)-Ryanodol

| Carbon No. | Authentic Ryanodol (from hydrolysis of ryanodine) Inoue, 2014 (ref. 29) (100 MHz, CD$_3$OD) $[\alpha]_D^{22} = +36$ (c 0.41, MeOH) $^{13}$C (δ) ppm | Synthetic (+)-Ryanodol (500 MHz, CD$_3$OD) $[\alpha]_D^{25}$: +37 (c = 0.30, MeOH) $^{13}$C (δ) ppm | Chemical Shift Difference, Δδ $^{13}$C (Δδ) ppm |
|---|---|---|---|
| 1 | 65.4 | 65.4 | 0 |
| 2 | 84.9 | 84.9 | 0 |
| 3 | 91.6 | 91.6 | 0 |
| 4 | 92.6 | 92.6 | 0 |
| 5 | 49.6 | 49.7 | 0.1 |
| 6 | 86.6 | 86.6 | 0 |
| 7 | 26.6 | 26.6 | 0 |
| 8 | 29.4 | 29.4 | 0 |
| 9 | 35.4 | 35.4 | 0 |
| 10 | 72.9 | 72.9 | 0 |
| 11 | 87.3 | 87.3 | 0 |
| 12 | 96.3 | 96.3 | 0 |
| 13 | 30.7 | 30.7 | 0 |
| 14 | 41.5 | 41.5 | 0 |
| 15 | 103.1 | 103.1 | 0 |
| 17 | 10.2 | 10.2 | 0 |
| 18 | 19.4 | 19.4 | 0 |
| 19 | 19.5 | 19.5 | 0 |
| 20 | 13.2 | 13.2 | 0 |
| 21 | 19.0 | 19.0 | 0 |

Example 20: X-Ray Structure Determination for 17

Crystals of 17 were grown by slow, repeated crystallization from Et$_2$O and found to be suitable for X-ray diffraction. Low-temperature diffraction data (φ- and ω-scans) were collected on a Bruker AXS D8 VENTURE KAPPA diffractometer coupled to a PHOTON 100 CMOS detector with Cu-Kα radiation (λ=1.54178 Å) from an I$_\mu$S microsource. All diffractometer manipulations, including data collection, integration, and scaling were carried out using the Bruker APEXII software (APEX2, Version 2 User Manual, M86-E01078, Bruker Analytical X-ray Systems, Madison, Wis., June 2006)). Absorption corrections were applied using SADABS (G. M. Sheldrick, "SADABS (version 2008/1): Program for Absorption Correction for Data from Area Detector Frames," University of Gottingen, Gottingen, Germany, 2008). The structure was solved by intrinsic phasing using SHELXT (Sheldrick, Acta Cryst., A-64, 112-122, 2008) and refined against F$^2$ on all data by full-matrix least squares with SHELXL-2014 using established refinement techniques and with an extinction correction of 0.00106(15) (Müller, Crystallogr. Rev., 15, 57-83, 2009). All non-hydrogen atoms were refined using anisotropic displacement parameters. All hydrogen atoms were included into the model at geometrically calculated positions and refined using a riding model. Compound 17 crystallizes in the orthorhombic space group P2$_1$2$_1$2$_1$ and absolute configuration was determined by anomalous dispersion (Flack=−0.02(8)) (Parsons et al., Acta Cryst., B69, 249-259, 2013). CCDC deposition number 1478621 contains the supplementary crystallographic data for 17. This data can be obtained free of charge from The Cambridge Crystallographic Data Centre via www.ccdc.cam.ac.uk/data_request/cif.

TABLE 4

Crystal data and structure refinement

| Empirical formula | $C_{33}H_{38}O_7$ | |
| Formula weight | 546.63 | |
| Temperature | 100 K | |
| Wavelength | 1.54178 Å | |
| Crystal system | Orthorhombic | |
| Space group | P2$_1$2$_1$2$_1$ | |
| Unit cell dimensions | a = 7.5193(3) Å | α = 90° |
| | b = 9.9691(4) Å | β = 90° |
| | c = 37.1447(17) Å | γ = 90° |

TABLE 4-continued

Crystal data and structure refinement

| | |
|---|---|
| Volume | 2784.4(2) Å³ |
| Z | 4 |
| Density (calculated) | 1.304 mg/m³ |
| Absorption coefficient | 0.735 mm⁻¹ |
| F(000) | 1168 |
| Crystal size | 0.22 × 0.15 × 0.12 mm³ |
| Theta range for data collection | 2.379 to 78.722° |
| Index ranges | $-9 <= h <= 8$, $-11 <= k <= 12$, $-44 <= l <= 46$ |
| Reflections collected | 25520 |
| Independent reflections | 5891 [R(int) = 0.0654] |
| Completeness to theta = 67.679° | 100.0% |
| Absorption correction | Semi-empirical from equivalents |
| Max. and min. transmission | 0.7542 and 0.6748 |
| Refinement method | Full-matrix least-squares on F² |
| Data/restraints/parameters | 5891/0/369 |
| Goodness-of-fit on F² | 1.054 |
| Final R indices [I > 2sigma(I)] | R1 = 0.0332, wR2 = 0.0756 |
| R indices (all data) | R1 = 0.0395, wR2 = 0.0783 |
| Absolute structure parameter | −0.02(8) |
| Extinction coefficient | 0.00106(15) |
| Largest diff. peak and hole | 0.388 and −0.305 e.Å⁻³ |

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document, including Chuang, Xu, and Reisman, "A 15-step Synthesis of (+)-Ryanodol," Science, 26 Aug. 2016, 353(6302):912-915, are hereby incorporated herein by reference, each in its entirety, for all purposes.

What is claimed:

1. A method for preparing a compound of Formula (I):

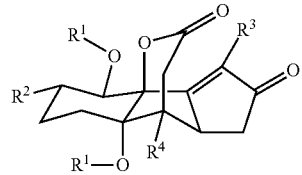

comprising subjecting a compound of Formula (II):

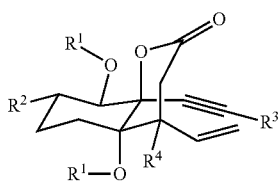

to a source of carbon monoxide in the presence of a catalyst, for a time and at a temperature sufficient to produce the compound of Formula (I);

wherein:

each $R^1$ is a reductively labile oxygen protecting group or an acid labile oxygen protecting group; and $R^2$ is $C_{1-6}$alkyl;

$R^3$ is $C_{1-6}$alkyl; and $R^4$ is $C_{1-6}$alkyl.

2. The method of claim 1, wherein each $R^1$ is —$CH_2$—O-benzyl.

3. The method of claim 1, wherein $R^2$ is $CH_3$.

4. The method of claim 1, wherein $R^3$ and $R^4$ are $CH_3$.

5. The method of claim 1, wherein the source of carbon monoxide is gaseous CO, $Co_2(CO)_8$, or $Mo(CO)_3(DMF)_3$.

6. The method of claim 1, wherein the catalyst is a rhodium catalyst.

7. The method of claim 1, wherein the compound of formula (I) is produced in a diastereomeric ratio of at least about 3:1.

8. The method of claim 1, wherein the compound of formula (I) is compound 17:

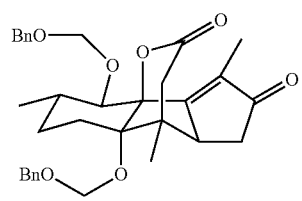

9. The method of claim 1, wherein the compound of formula (II) is compound 16:

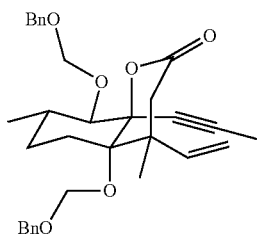

10. The method of claim 1, further comprising subjecting the compound of formula (I) to an oxidant, in an organic solvent, for a time and at a temperature sufficient to form a compound of formula (III):

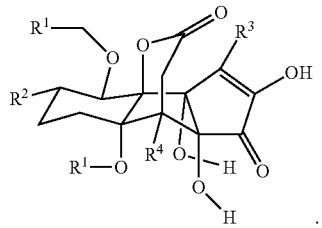

11. The method of claim 10, wherein the oxidant is selenium dioxide or molecular oxygen.

12. The method of claim 10, wherein the organic solvent is anhydrous.

13. The method of claim 10, wherein the compound of formula (III) is compound 18:

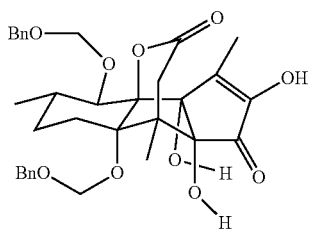

14. The method of claim 10, further comprising treating the compound of formula (III) with a triflating agent to form a compound of formula (IV):

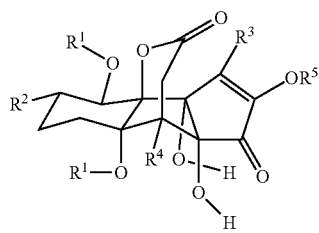

wherein $R^5$ is Tf (—$SO_2CF_3$).

15. The method of claim 14, wherein the triflating agent is N-(5-chloro-2-pyridyl) bis(trifluoromethanesulfonimide).

16. The method of claim 14, wherein the compound of formula (IV) is compound 19:

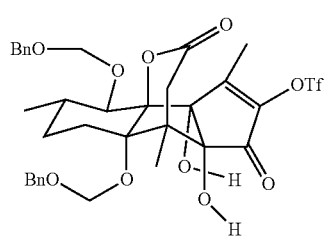

17. The method of claim 14, further comprising treating the compound of formula (IV) with $R^6C(=CH_2)Sn(C_{1-6}alkyl)_3$ in the presence of a catalyst to provide a compound of formula (V):

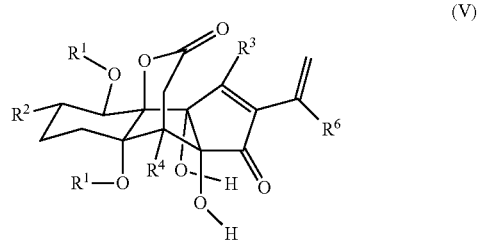

wherein $R^6$ is $C_{1-6}$alkyl.

18. The method of claim 17, wherein $R^6C(=CH_2)Sn(C_{1-6}alkyl)_3$ is $CH_3C(=CH_2)SnBu_3$.

19. The method of claim 17, wherein the catalyst is a palladium catalyst.

20. The method of claim 17, wherein the catalyst is $PdCl_2(PPh_3)_2$.

21. The method of claim 17, wherein the compound of formula (V) is compound 20:

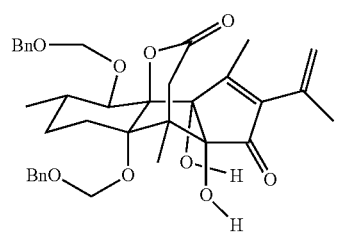

22. The method of claim 17, further comprising treating the compound of formula (V) with one or more reducing agents, and optionally a catalyst, for a time and at a temperature sufficient to provide a compound of formula (VI):

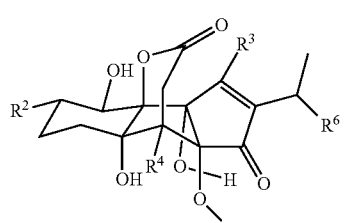

23. The method of claim 22, wherein the reducing agent is a hydride, hydrogen, or a mixture thereof.

24. The method of claim 22, wherein the reducing agent is lithium borohydride.

25. The method of claim 22, wherein the reducing agent is hydrogen.

26. The method of claim 22, wherein the catalyst is a palladium catalyst.

27. The method of claim 26, wherein the catalyst is Pd(OH)$_2$/C.

28. The method of claim 22, wherein the compound of formula (VI) is compound 3:

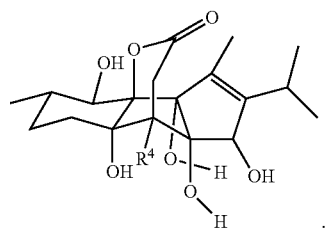

29. The method of claim 22, further comprising:
(i) reacting the compound of formula (VI) with trifluoroperacetic acid; and
(ii) reacting the compound of step (i) with lithium metal in liquid ammonia to provide a compound of formula (VII):

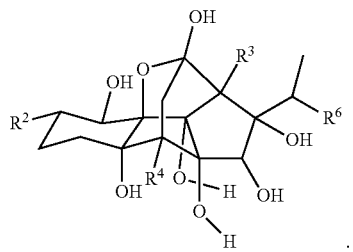

30. The method of claim 29, wherein the compound of formula (VII) is compound 2:

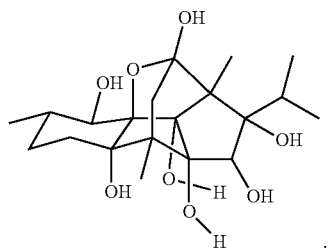

31. The method of claim 29, wherein the compound of formula (VII) is (+)-ryanodol.

32. The method of claim 6, wherein the rhodium catalyst is [RhCl(CO)$_2$]$_2$.

* * * * *